US010394776B2

(12) United States Patent
Khan

(10) Patent No.: US 10,394,776 B2
(45) Date of Patent: *Aug. 27, 2019

(54) WARNING SYSTEM FOR INFECTIOUS DISEASES AND METHOD THEREFOR

(71) Applicant: BIODIASPORA INC., Toronto (CA)

(72) Inventor: Kamran Khan, Toronto (CA)

(73) Assignee: BlueDot Inc., Toronto (CA)

( * ) Notice: Subject to any disclaimer, the term of this patent is extended or adjusted under 35 U.S.C. 154(b) by 1256 days.

This patent is subject to a terminal disclaimer.

(21) Appl. No.: 14/378,376

(22) PCT Filed: Feb. 13, 2013

(86) PCT No.: PCT/CA2013/050110
§ 371 (c)(1),
(2) Date: Aug. 13, 2014

(87) PCT Pub. No.: WO2013/120199
PCT Pub. Date: Aug. 22, 2013

(65) Prior Publication Data
US 2015/0012292 A1 Jan. 8, 2015

Related U.S. Application Data

(60) Provisional application No. 61/598,024, filed on Feb. 13, 2012.

(51) Int. Cl.
*G06Q 10/04* (2012.01)
*G06F 16/22* (2019.01)
(Continued)

(52) U.S. Cl.
CPC ........ *G06F 16/2228* (2019.01); *G06F 16/904* (2019.01); *G06F 19/00* (2013.01);
(Continued)

(58) Field of Classification Search
CPC .................... G06Q 50/22; G06Q 50/24; G06F 19/322–327
See application file for complete search history.

(56) References Cited

U.S. PATENT DOCUMENTS 6,838,993 B2 * 1/2005 Beiswenger ........... G16H 50/80
340/573.5

OTHER PUBLICATIONS

Google patents search, Mar. 31, 2019 (Year: 2019).*
(Continued)

*Primary Examiner* — Dilek B Cobanoglu
(74) *Attorney, Agent, or Firm* — McMillan LLP

(57) ABSTRACT

A method and a system for predicting the local area impact of the spread of global infectious diseases are provided. The system includes: providing a global pathogen risk factors database having data related to local area vulnerability of a group of human pathogens across a plurality of areas, a global pathogen activity database having data related to the activity of the group of human pathogens in the plurality of geographies, and a global transport database having data related to travel patterns in and/or between the plurality of areas. A method of processing data in each of the databases to generate a pathogen vulnerability index, a pathogen activity index and a transportability index to generate a risk indicator indicative of the local area impact of individual global infectious diseases.

24 Claims, 23 Drawing Sheets

(51) Int. Cl.
    *G06Q 50/22*      (2018.01)
    *G16H 50/30*      (2018.01)
    *G16H 50/80*      (2018.01)
    *G06F 19/00*      (2018.01)
    *G06F 16/904*    (2019.01)

(52) U.S. Cl.
    CPC .............. *G06Q 10/04* (2013.01); *G06Q 50/22* (2013.01); *G16H 50/30* (2018.01); *G16H 50/80* (2018.01); *Y02A 90/22* (2018.01); *Y02A 90/24* (2018.01); *Y02A 90/26* (2018.01)

(56) References Cited

OTHER PUBLICATIONS

Khan et al. "Preparing for infectious disease threats at mass gatherings the case of the Vancouver 2010 Olympic Winter Games". CMAJ vol. 182. No. 6. pp. 579-583. Feb. 24, 2010.

Huang et al. "A multilayer epidemic simulation framework integrating geographic information system with traveling networks". Proceedings of the 8th World Congress on Intelligent Control and Automation (WCICA). pp. 2002-2007. Jul. 2010.

Duczmal et al. "A Voronoi based scan for space-time cluster detection in point event data". International Society for Disease Surveillance Conference 2011. pp. 18-19. Dec. 6, 2011.

* cited by examiner

*Figure 4*

| INFECTIOUS DISEASE | CHOLERA |
|---|---|
| Type of infectious agent | Bacterium |
| Communicable | Yes |
| Estimated reproduction number | 2-3 |
| Potential biological weapon | Yes |
| Bioterrorism category | B |
| Incubation period (range) | 2 hours to 5 days |
| Incubation period (average) | 2-3 days |
| Acute morbidity (severe illness among all symptomatic cases) | Intermediate (5-10%) |
| Acute mortality (death among all symptomatic cases) | Low (< 1%) |
| Acute mortality (death among severe symptomatic cases) | High (30-50%) |
| Vaccine | Limited special access |
| Pre-exposure prophylaxis | Unproven benefit |
| Post-exposure prophylaxis | Unproven benefit |
| Antimicrobials for disease | Proven benefit |
| Antimicrobial resistance | Sporadic |
| Zoonosis | No |
| Vector borne | No |
| Risk factors for infection | Inadequate water treatment and sanitation systems |
| Risk factors for severe illness | Compromised immunity<br>• HIV-AIDS<br>• Malnutrition<br>• Extremes of age |
| Environmental reservoir | Aquatic environments<br>Infected humans |
| Sources of human infections | Infected humans<br>Raw or undercooked shellfish |
| Primary mode(s) of transmission | Fecal-Oral<br>• Water-borne<br>• Food-borne |

*Figure 15*

| Geography (Voronoi) | Population Density (people/km2) | Population Access to Clean Water (%) | Population Access to Enhanced Sanitation (%) | Population Prevalence of HIV-AIDS (%) | Precipitation in Past 7 Days (mm) | Healthcare Resources ($ per capita) | Physician Supply (Physicians per 1000 people) | | |
|---|---|---|---|---|---|---|---|---|---|
| Aalborg | 194 | 100 | 100 | 0.2 | 17 | 4,125 | 1.2 | | |
| Aalesund | 76 | 100 | 100 | 0.1 | 9 | 4,076 | 1.4 | | |
| Aarhus | 47 | 100 | 99 | 0.2 | 31 | 5,789 | 1.2 | | |
| Aasiaat | 12 | 93 | 88 | 0.4 | 45 | 341 | 0.2 | | |
| Abadan | 609 | 89 | 86 | 0.5 | 8 | 256 | 0.6 | | |
| Abakan | 105 | 97 | 98 | 0.4 | 68 | 153 | 1.1 | | |
| Abbotsford | 296 | 100 | 99 | 0.4 | 26 | 4,694 | 2.1 | | |
| Abecher | 97 | 84 | 87 | 1.1 | 11 | 68 | 0.5 | | |
| Abeokuta | 548 | 85 | 81 | 1.7 | 7 | 45 | 0.6 | | |
| Aberdeen (US) | 305 | 100 | 99 | 0.5 | 25 | 6,199 | 4.1 | | |
| Aberdeen (GB) | 403 | 100 | 100 | 0.2 | 13 | 5,784 | 2.9 | | |
| Abha | 148 | 95 | 97 | 0.0 | 0 | 1193 | 1.8 | | |
| Abidjan | 1138 | 83 | 80 | 1.3 | 44 | 88 | 0.9 | | |
| Abilene | 224 | 99 | 99 | 0.3 | 24 | 5784 | 4.1 | | |
| Abu Dhabi | 954 | 99 | 97 | 0.4 | 2 | 1532 | 3.0 | | |
| Abu Musa | 286 | 89 | 91 | 0.2 | 21 | 256 | 0.6 | | |

*Figure 16*

| Geography (Voronoi) | Population Density (people/km2) | Population Access to Clean Water (%) | Population Access to Enhanced Sanitation (%) | Population Prevalence of HIV-AIDS (%) | Precipitation in Past 7 Days (mm) | Healthcare Resources ($ per capita) | Physician Supply (Physicians per 1000 people) | Cumulative Cholera Vulnerability Index | Rescaled Cumulative Cholera Vulnerability Index |
|---|---|---|---|---|---|---|---|---|---|
| Aalborg | 0.15 | 0.0 | 0.0 | 0.2 | 0.05 | 0.03 | 0.03 | 0.46 | 0.03 |
| Aalesund | 0.02 | 0.0 | 0.0 | 0.02 | 0.03 | 0.04 | 0.05 | 0.16 | 0.01 |
| Aarhus | 0.01 | 0.0 | 0.01 | 0.03 | 0.29 | 0.01 | 0.04 | 0.39 | 0.02 |
| Aasiaat | 0.01 | 0.18 | 0.12 | 0.07 | 0.43 | 0.67 | 0.46 | 1.94 | 0.31 |
| Abadan | 0.67 | 0.24 | 0.19 | 0.08 | 0.02 | 0.75 | 0.06 | 2.01 | 0.34 |
| Abakan | 0.07 | 0.04 | 0.03 | 0.32 | 0.68 | 0.84 | 0.07 | 2.05 | 0.35 |
| Abbotsford | 0.42 | 0.0 | 0.01 | 0.03 | 0.24 | 0.03 | 0.04 | 0.77 | 0.09 |
| Abecher | 0.07 | 0.25 | 0.17 | 0.72 | 0.03 | 0.97 | 0.86 | 3.07 | 0.57 |
| Abeokuta | 0.63 | 0.23 | 0.45 | 0.92 | 0.01 | 0.98 | 0.91 | 4.13 | 0.68 |
| Aberdeen (US) | 0.32 | 0.0 | 0.01 | 0.04 | 0.18 | 0.0 | 0.01 | 0.56 | 0.03 |
| Aberdeen (GB) | 0.39 | 0.0 | 0.0 | 0.02 | 0.02 | 0.01 | 0.06 | 0.50 | 0.03 |
| Abha | 0.21 | 0.02 | 0.04 | 0.0 | 0 | 0.31 | 0.23 | 0.81 | 0.14 |
| Abidjan | 0.81 | 0.23 | 0.58 | 0.74 | 0.38 | 0.91 | 0.82 | 4.47 | 0.88 |
| Abilene | 0.31 | 0.01 | 0.01 | 0.08 | 0.21 | 0.0 | 0.01 | 0.63 | 0.06 |
| Abu Dhabi | 0.73 | 0.01 | 0.04 | 0.06 | 0.01 | 0.34 | 0.02 | 1.21 | 0.26 |
| Abu Musa | 0.34 | 0.36 | 0.09 | 0.11 | 0.19 | 0.86 | 0.32 | 2.27 | 0.38 |

*Figure 17*

| Geography (Voronoi) | Reported Cholera Incidence (cases per 100,000 people) | Online Media Activity re Cholera (News Reports in Past 7 Days) | Pro-MED Mail Activity re Cholera (Alerts in Past 7 Days) | Social Media Activity re Cholera (Tweets per Capita in Past 7 Days) | Google Search Activity re Cholera (Searches per Capita in Past 7 Days) | | |
|---|---|---|---|---|---|---|---|
| Aalborg | 0 | 0 | 0 | 0 | 0.11 | | |
| Aalesund | 0 | 0 | 0 | 0 | 0.04 | | |
| Aarhus | 0 | 0 | 0 | 0 | 0.01 | | |
| Aasiaat | 0 | 0 | 0 | 0 | 0.02 | | |
| Abadan | 5.2 | 0 | 0 | 0 | 0.01 | | |
| Abakan | 1.1 | 0 | 0 | 0 | 0.01 | | |
| Abbotsford | 0 | 0 | 0 | 0 | 0.02 | | |
| Abecher | 28.3 | 1 | 0 | 0.1 | 0.01 | | |
| Abeokuta | 112.6 | 14 | 2 | 0.4 | 0.5 | | |
| Aberdeen (US) | 0 | 0 | 0 | 0 | 0.1 | | |
| Aberdeen (GB) | 0 | 0 | 0 | 0 | 0.2 | | |
| Abha | 0.7 | 0 | 0 | 0 | 0.01 | | |
| Abidjan | 24.4 | 3 | 1 | 0.04 | 0.24 | | |
| Abilene | 0 | 0 | 0 | 0 | 0.01 | | |
| Abu Dhabi | 0.2 | 0 | 0 | 0 | 0.02 | | |
| Abu Musa | 5.2 | 0 | 0 | 0.001 | 0.01 | | |

*Figure 18*

| Geography (Voronoi) | Reported Cholera Incidence (cases per 100,000 people) | Online Media Activity re Cholera (News Reports in Past 7 Days) | Pro-MED Mail Activity re Cholera (Alerts in Past 7 Days) | Social Media Activity re Cholera (Tweets per Capita in Past 7 Days) | Google Search Activity re Cholera (Searches per Capita in Past 7 Days) | Cumulative Cholera Activity Index | Rescaled Cumulative Cholera Activity Index |
|---|---|---|---|---|---|---|---|
| Aalborg | 0.0 | 0.0 | 0.0 | 0.0 | 0.26 | 0.26 | 0.31 |
| Aalesund | 0.0 | 0.0 | 0.0 | 0.0 | 0.09 | 0.09 | 0.11 |
| Aarhus | 0.0 | 0.0 | 0.0 | 0.0 | 0.01 | 0.01 | 0.01 |
| Aasiaat | 0.0 | 0.0 | 0.0 | 0.0 | 0.05 | 0.05 | 0.03 |
| Abadan | 0.24 | 0.0 | 0.0 | 0.0 | 0.01 | 0.25 | 0.43 |
| Abakan | 0.12 | 0.0 | 0.0 | 0.0 | 0.01 | 0.13 | 0.18 |
| Abbotsford | 0.0 | 0.0 | 0.0 | 0.0 | 0.05 | 0.05 | 0.03 |
| Abecher | 0.74 | 0.47 | 0.0 | 0.51 | 0.01 | 1.73 | 0.78 |
| Abeokuta | 0.91 | 0.86 | 0.78 | 0.83 | 0.91 | 4.29 | 0.95 |
| Aberdeen (US) | 0.0 | 0.0 | 0.0 | 0.0 | 0.19 | 0.19 | 0.23 |
| Aberdeen (GB) | 0.0 | 0.0 | 0.0 | 0.0 | 0.32 | 0.32 | 0.37 |
| Abha | 0.05 | 0.0 | 0.0 | 0.0 | 0.01 | 0.06 | 0.07 |
| Abidjan | 0.67 | 0.56 | 0.57 | 0.09 | 0.67 | 2.56 | 0.85 |
| Abilene | 0.0 | 0.0 | 0.0 | 0.0 | 0.01 | 0.01 | 0.01 |
| Abu Dhabi | 0.02 | 0.0 | 0.0 | 0.0 | 0.04 | 0.06 | 0.05 |
| Abu Musa | 0.24 | 0.0 | 0.0 | 0.01 | 0.01 | 0.26 | 0.31 |

*Figure 19*

| Airline Travelers in Past 7 Days Columns - Origin Rows - Destination | Aalborg | Aalesund | Aarhus | Aasiaat | Abadan | Abakan | Abbotsford Etc. |
|---|---|---|---|---|---|---|---|
| Aalborg | --- | 411 | 1134 | 34 | 3 | 13 | 8 |
| Aalesund | 376 | --- | 1532 | 24 | 0 | 4 | 16 |
| Aarhus | 964 | 342 | --- | 11 | 2 | 8 | 0 |
| Aasiaat | 17 | 7 | 14 | --- | 5 | 43 | 0 |
| Abadan | 0 | 1 | 0 | 6 | --- | 143 | 4 |
| Abakan | 5 | 14 | 7 | 2 | 113 | --- | 7 |
| Abbotsford Etc. | 28 | 14 | 13 | 0 | 2 | 14 | --- |

*Figure 20*

| Transportability Index (Past 7 Days) Columns - Origin Rows - Destination | Aalborg | Aalesund | Aarhus | Aasiaat | Abadan | Abakan | Abbotsford |
|---|---|---|---|---|---|---|---|
| Aalborg | --- | 0.95 | 0.72 | 0.11 | 0.01 | 0.06 | 0.12 |
| Aalesund | 0.54 | --- | 0.83 | 0.07 | 0.0 | 0.02 | 0.31 |
| Aarhus | 0.81 | 0.91 | --- | 0.03 | 0.01 | 0.04 | 0.0 |
| Aasiaat | 0.21 | 0.03 | 0.07 | --- | 0.02 | 0.21 | 0.0 |
| Abadan | 0.0 | 0.01 | 0.0 | 0.02 | --- | 0.41 | 0.01 |
| Abakan | 0.03 | 0.13 | 0.03 | 0.01 | 0.67 | --- | 0.03 |
| Abbotsford | 0.24 | 0.13 | 0.07 | 0.0 | 0.01 | 0.13 | --- |

*Figure 21*

| Geography (Voronoi) | Rescaled Cumulative Cholera Activity Index (User Weighted) | Transportability Index (into Addis Ababa) |
|---|---|---|
| Aalborg | 0.25 | 0.02 |
| Aalesund | 0.18 | 0.03 |
| Aarhus | 0.0 | 0.01 |
| Aasiaat | 0.05 | 0.0 |
| Abadan | 0.49 | 0.24 |
| Abakan | 0.24 | 0.11 |
| Abbotsford | 0.05 | 0.02 |
| Abecher | 0.81 | 0.01 |
| Abeokuta | 0.98 | 0.05 |
| Aberdeen (US) | 0.25 | 0.03 |
| Aberdeen (GB) | 0.38 | 0.12 |
| Abha | 0.07 | 0.04 |
| Abidjan | 0.81 | 0.26 |
| Abilene | 0.01 | 0.02 |
| Abu Dhabi | 0.06 | 0.28 |
| Abu Musa ↓ | 0.25 | 0.03 |

WARNING SYSTEM FOR INFECTIOUS DISEASES AND METHOD THEREFOR

RELATED APPLICATIONS

This application claims priority to U.S. Provisional Patent Application No. 61/598,024 filed Feb. 13, 2012, the contents of which are herein expressly incorporated by reference.

FIELD OF THE INVENTION

The invention relates to a warning system for infectious diseases, including a global early warning system for infectious diseases and method therefor, and in particular to a system for forecasting the local risks and consequences of global infectious diseases, and method therefor.

BACKGROUND OF THE INVENTION

New, previously unknown or unrecognized human pathogens are emerging faster than ever before. Furthermore, many existing human pathogens are evolving into new and potentially dangerous forms. At the same time, the world is becoming increasingly interconnected by air travel. Today more than 2.5 billion travelers board commercial flights every year, creating unprecedented opportunities for locally occurring infectious disease events to rapidly transform into international epidemics or global pandemics. Events such as the worldwide SARS outbreak in 2003 and the H1N1 pandemic in 2009 have clearly demonstrated the ease with which pathogens can spread across international borders and threaten human health, security, and economic activity.

Recent technological innovations to confront emerging global infectious diseases have focused on the early detection of potential threats through real-time analysis of massive volumes of Internet data. These innovations include software systems that analyze mass media content (e.g. online news), social media content (e.g. Twitter™), search engine activity (e.g. Google™ Flu trends), and other online communication channels for signs of potentially dangerous infectious diseases around the world. Recently, some of these systems have been coupled with information on global air traffic patterns to predict how a known human pathogen in a specific geography might spread around the world (see FIG. 1). These systems, which predict how individual infectious disease threats disseminate globally from a single geography at a defined moment in time, are incapable of forecasting or anticipating how a global array of infectious disease threats present risks to every geography in the world on a continuous real-time basis. There is therefore a need in the art for an improved method and system that is anticipatory in nature, which can forecast the local risks and consequences of continuously evolving global infectious disease activity.

SUMMARY OF THE INVENTION

According to one embodiment of the invention, there is disclosed a computer implemented method for predicting local area risks of global infectious diseases including providing on a computer readable medium a global pathogen risk factors database having data stored therein related to local area vulnerability of individual human pathogens across a plurality of areas, providing on a computer readable medium a global pathogen activity database having data stored therein related to local area activity of the individual human pathogens in said plurality of areas, providing on a computer readable medium a global transport database having data stored therein related to human travel patterns in and/or between a plurality of the local areas, processing by a computer system data on each of the global pathogen risk factors database, the global pathogen activity database and the global transport database to generate a pathogen vulnerability index, a pathogen activity index and a transportability index, and processing by the computer system each of the pathogen vulnerability index, the pathogen activity index and the transportability index to generate a local area risk indicator for individual global infectious diseases.

According to one aspect of the invention, there is further provided a step of modeling by the computer system each of the plurality of areas as a spatial unit.

According to another aspect of the invention, the plurality of areas comprises all cities in the world having at least one airport, such that there is stored a unique spatial unit for each the city with at least one airport.

According to another aspect of the invention, each spatial unit is a function of each city's proximity to neighboring cities with at least one airport and of the corresponding magnitude of air traffic at each airport.

According to another aspect of the invention, the spatial unit is a Voronoi polygon, other polygon, or any other geographic unit.

According to another aspect of the invention, the method further includes normalizing by the computer system values in the global pathogen risk factors database, the global pathogen activity database and the global transport database.

According to another aspect of the invention, the pathogen vulnerability index the pathogen activity index and the transportability index are also aggregated and normalized into a single unweighted or weighted cumulative risk index.

According to another aspect of the invention, the normalizing comprises scaling to a value between 0 and 1.

According to another aspect of the invention, the data stored on the global pathogen risk factors database related to the local area vulnerability of individual human pathogens includes a list of individual risks and risk factors applied to each of the individual risks; and wherein the generating of a cumulative pathogen vulnerability index comprises assigning and scaling an index to each of the one or more risk factors for each pathogen and then calculating an average or weighted average.

According to another aspect of the invention, the list of individual risks and risk factors are further provided for each pathogen in the group of human pathogens.

According to another aspect of the invention, the data stored in the global pathogen activity database includes worldwide data on the activity of pathogens derived from one or more different sources.

According to another aspect of the invention, the one or more different sources are selected from the group comprising official government reporting, reporting from medical and public health professional networks, mass media news sources, portable diagnostic devices, mobile applications, Internet search activity and social media.

According to another aspect of the invention, the generating of a cumulative pathogen activity index comprises assigning and scaling an index to each of the one or more different information sources for each pathogen and then calculating an average or a weighted average.

According to another aspect of the invention, the transportability index is calculated by assigning a geography index between each and every city based on the number of inbound travelers expected to arrive.

According to another embodiment of the invention, there is provided a computer system for predicting the local area risks of global infectious diseases including a computer readable medium having a global pathogen risk factors database with data stored therein related to local area vulnerability of individual human pathogens across a plurality of areas, a computer readable medium having a global pathogen activity database having data stored therein related to the local area activity of the individual human pathogens in said plurality of areas, a computer readable medium having a global transport database including data stored therein related to human travel patterns in and/or between the plurality of local areas, computer executable instructions executed by the computer system for processing by a computer system data on each of the global pathogen risk factors database, the global pathogen activity database and the global transport database to generate a pathogen vulnerability index, a pathogen activity index and a transportability index, and computer executable instructions executed by the computer system for processing by the computer system each of the pathogen vulnerability index, the pathogen activity index and the transportability index to generate a local area risk indicator for individual global infectious diseases.

According to another aspect of the second embodiment, the system includes computer executable instructions for carrying out the method as herein described.

BRIEF DESCRIPTION OF THE DRAWINGS

An embodiment will now be described, by way of example only, with reference to the attached Figures, wherein:

FIG. 4 shows an exemplary pathogen profile used in embodiments of the invention.

FIG. 15 shows a table of selected risk factor values for cholera used to generate vulnerability indices for individual cities.

FIG. 16 shows a table with rescaled risk factor values for cholera and cumulative vulnerability indices for individual cities.

FIG. 17 shows a table of selected surveillance data values for cholera used to generate activity indices for individual cities.

FIG. 18 shows a table with rescaled surveillance data values for cholera and cumulative activity indices for individual cities.

FIG. 19 shows a table with inbound airline traffic values between city pairs.

FIG. 20 shows a table with rescaled inbound airline traffic values as transportability indices between city pairs.

FIG. 21 shows a table of cholera activity indices worldwide and transportability indices worldwide in to Addis Ababa to depict the risk of cholera importation.

DESCRIPTION OF THE PREFERRED EMBODIMENTS

A novel system and method to create a real-time global early warning system for infectious diseases in accordance with an embodiment of the invention will now be described. The system continuously identifies risks from each major human pathogen to each city in the world—at any moment in time—by finding the spatiotemporal convergence of, inter alia, global, local, and pathogen-specific risk factors that could impact the health of a population.

Broadly, the hereinafter described invention provides for real-time systems that can continuously integrate and proactively synthesize knowledge of: i) worldwide vulnerability to individual pathogens, ii) worldwide activity of individual pathogens, and iii) worldwide connectivity through travel that could spread pathogens between global geographies. Synthesized intelligence from the invention could then be used by cities around the world in real-time to anticipate, and consequently prevent or mitigate, the local risks and consequences of infectious disease threats before they occur.

To this end, the system of the invention dynamically produces three indices or scores, which in combination offers all cities with at least one airport the ability to understand their local vulnerability to individual human pathogens, and their associated risk of importation of those pathogens from other parts of the world. While the description refers to cities in the world, it will be understood by a person skilled in the art that the invention may be implemented in a subset of cities, or in a predefined geographical area.

Figure 1:
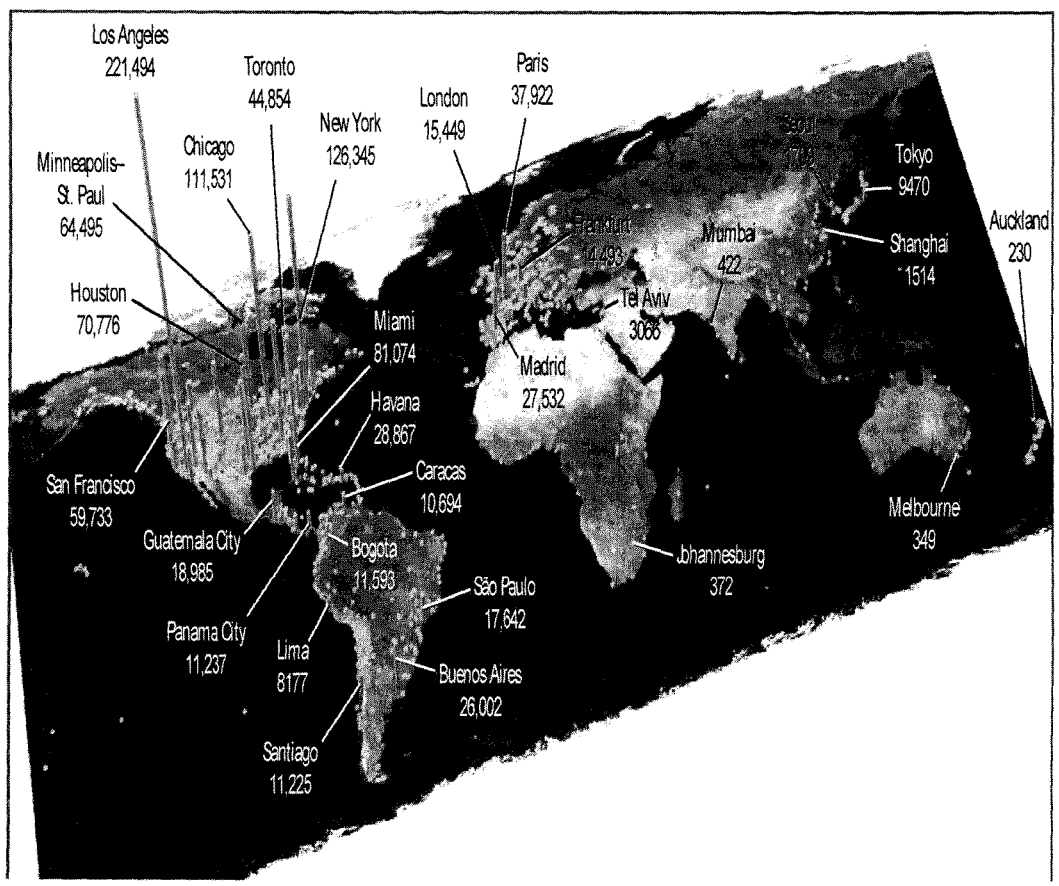
FIG. 1 shows the results of a prior art method showing world travel at the onset of the 2009 H1N1 pandemic.
Figure 2A:
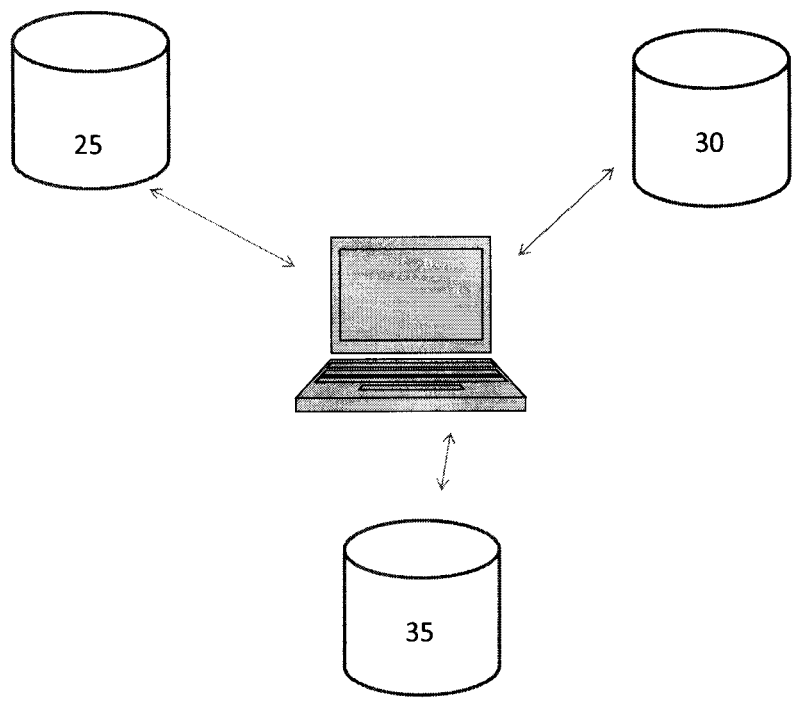
FIG. 2a shows a schematic of a system for carrying out the method according to the invention.
Figure 2B:
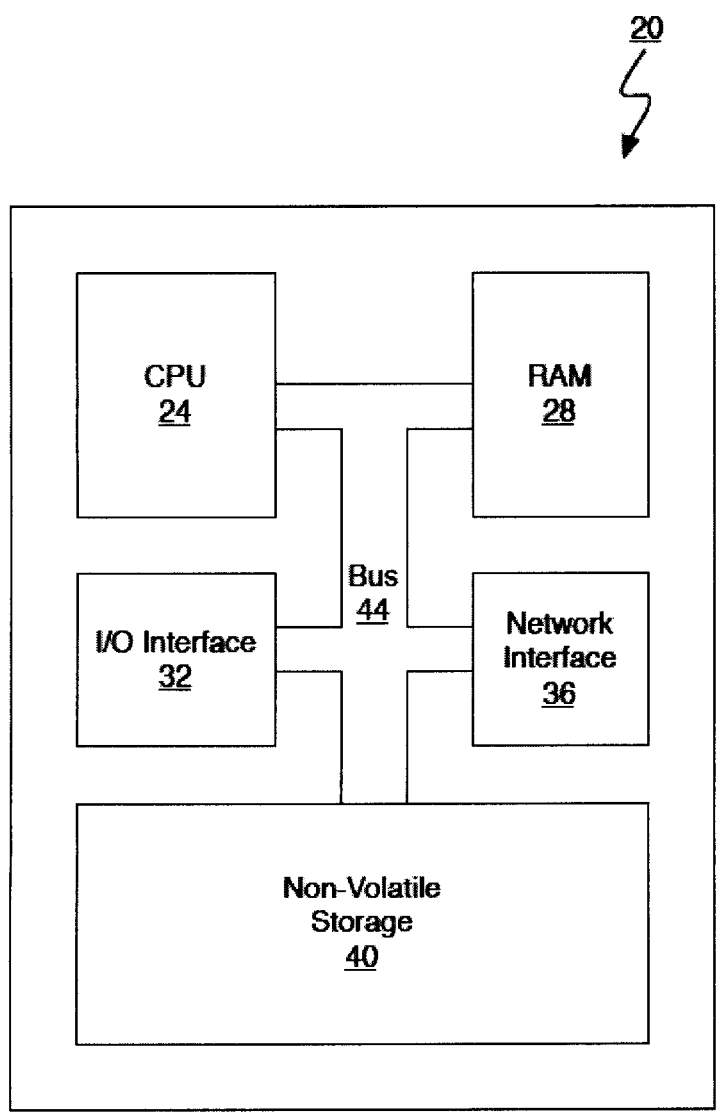
FIG. 2b shows a computer system that may be used to implement aspects of the invention.

Referring now to FIGS. 2a and 2b, there is shown a high-level system in which the invention may be implemented. As shown in the system of FIG. 2a, a global pathogen risk factors database 25 is provided on a computer readable medium, and accessible via a computer system. Similarly, a global pathogen activity database 30 and a global transport database 35 are provided. Each of these may be provided on a single computer readable medium and accessed by a single computer system, or on a plurality of computer data stores or computer systems. In this regard, FIG. 2b shows a computer system which may be used to implement the system described above, and includes a number of physical and logical components, including a central processing unit ("CPU") 24, random access memory ("RAM") 28, an input/output ("I/O") interface 32, a network interface 36, non-volatile storage 40, and a local bus 44 enabling the CPU 24 to communicate with the other components. The CPU 24 executes an operating system, and a number of software systems and/or software modules. RAM 28 provides relatively-responsive volatile storage to the CPU 24. The I/O interface 32 allows for input to be received from one or more devices, such as a keyboard, a mouse, a touch enabled device etc., and outputs information to output devices, such as a display. The network interface 36 permits communication with other elements of the invention described herein as being in networked communication with each other. Non-volatile storage 40 stores the operating system and programs. During operation of the computer system, the operating system, the programs and the data may be retrieved from the non-volatile storage 40 and placed in RAM 28 to facilitate execution.

Figure 5:
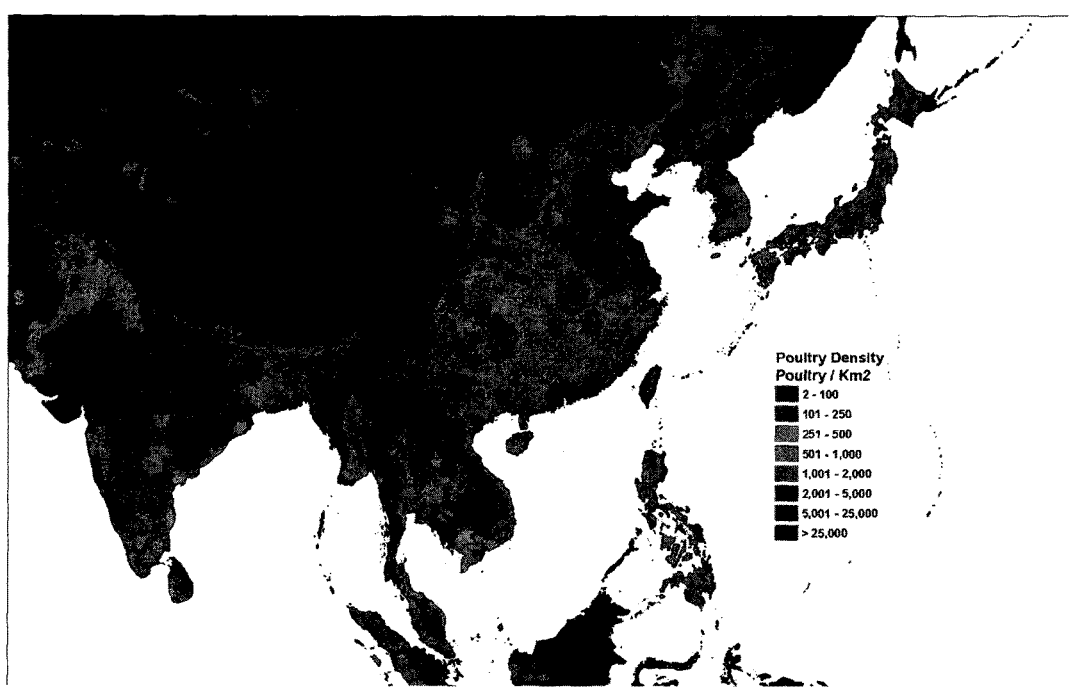
FIG. 5 shows the distribution and density of poultry populations across East Asia.
Figure 6:
FIG. 6 shows the global distribution of relative humidity.

First, the global pathogen risk factors database 25 is preferably populated with human, pathogen, environmental and medical diagnostic and therapeutic features of important human pathogens. An example of an entry in the global pathogen risk factors database is show in FIG. 4. FIGS. 5 and 6 show examples of environmental data that may be used, including the presence of an essential animal in the pathogen life cycle (such as poultry in the case of avian flu) and environmental humidity (such as in the case of influenza).

The global pathogen activity database 30 is preferably populated with one or more of the following pertaining to each pathogen: official government notifiable disease surveillance data, online real-time news (e.g. GPHIN, HealthMap, MediSys), communications from medical and public health professional networks (e.g. Pro-MED mail), real-time social media content, test results from point of care diagnostic devices, self-reported syndromes inputted via mobile health web-applications, and Internet search engine activity (e.g. Google™ Flu Trends). For definition purposes, variants of the same microorganism (i.e. such as a drug resistant or highly pathogenic form) are considered unique pathogens.

Finally, the global transport database is preferably is populated with data on worldwide flight schedules (e.g. Official Airline Guide), worldwide airline passenger ticket sales and flight itineraries (e.g. International Air Transport Association), and real-time aircraft-level flight data (e.g. FlightStats).

Figure 3:
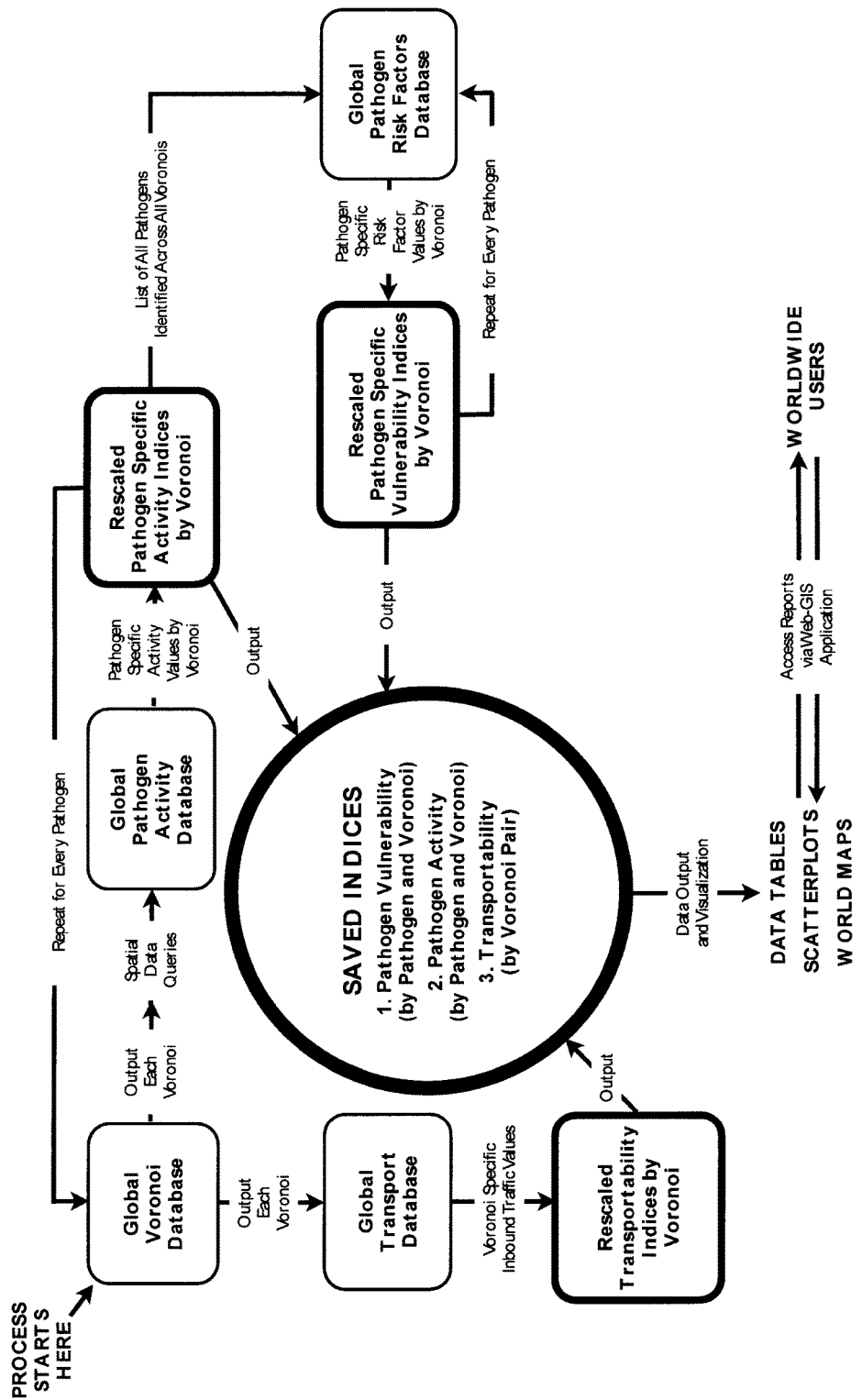
FIG. 3 shows the method according to an embodiment of the invention.

Each of the above-described databases and computer systems will now be described in more detail, along with details of implementation of the various aspects and features contemplated by the invention. Referring also to FIG. 3, the relationship between each of the databases, and a method according to the invention is also illustrated. As will now be apparent to a person skilled in the art, the invention takes advantage of pathogen vulnerability assessments, pathogen activity assessments and transportability assessments in deriving an index or score for each of these. It is also contemplated that an unweighted or weighted cumulative index or score would be derived. The cumulative index, specific to each pathogen and each city with at least one airport in the world, may then be used as an overall indicator for assessing or forecasting the local risks of global infectious diseases.

In one example, standardized indices are created from pathogen risk factor, pathogen activity and transportability databases by rescaling or normalizing all dataset values associated with each pathogen and human travel to a defined city. For example, in the case of vulnerability to cholera, population access to clean water percentages for each city in the world are transformed into relative values for each city that are scaled between 0 and 1. These indices are produced by accessing stored data from memory in the above databases, using computer processors to analyze datasets by applying predefined statistical rescaling algorithms, and then storing calculated results to computer memory. This process is repeated at frequent scheduled intervals. The steps involved in producing each of these indices are depicted in FIG. 3 and are described in detail below. For any pathogen at any point in time, each of the above three indices are combined to offer every city in the world with intelligence about their local vulnerability to that pathogen and its associated risk of importation from other parts of the world. The invention then produces and publishes secure reports on these risks to share with end-users using a combination of visualization methods including data tables and static or animated charts, graphs, and maps.

As a precursor to the generating of the indices mentioned above, creating a spatial unit for analysis is required, which is then used to define local areas within the overall geography being analyzed, which in the preferred embodiment is the world as a whole.

Creating a Spatial Unit for Analysis

Figure 7:
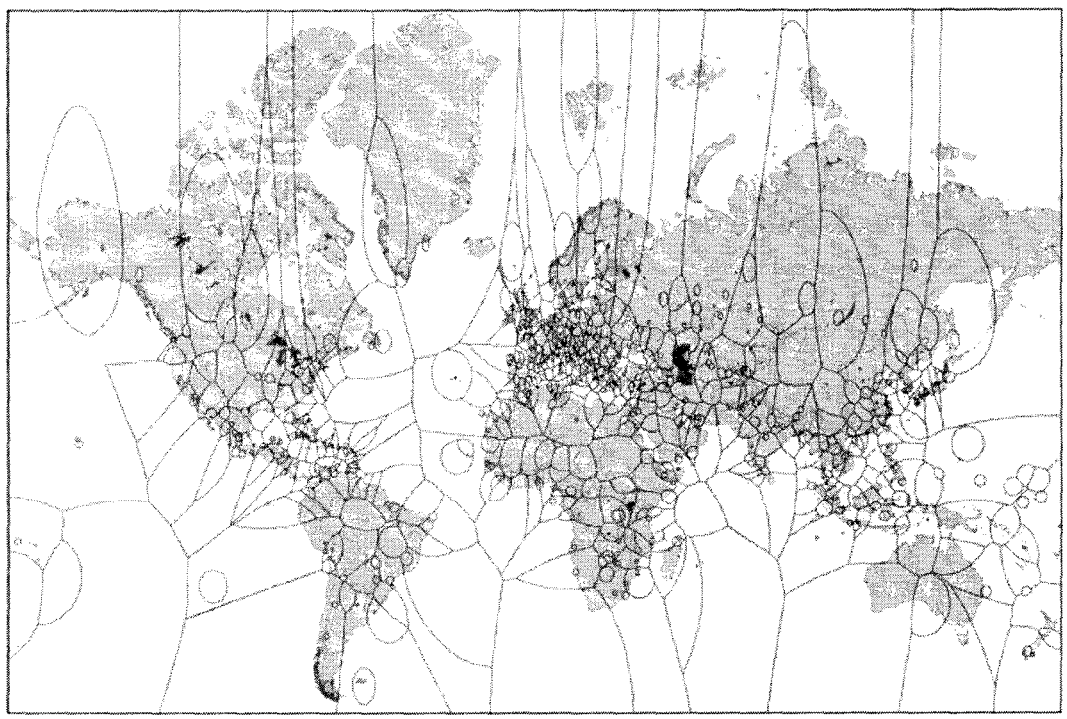
FIG. 7 shows the world modeled using weighted Voronoi polygons.

One way in which a spatial unit can be created is by way of the use of Voronoi polygons. According to the preferred embodiment, Voronoi polygons are created to deconstruct the world's land geography into distinct areas around cities with airports, which then serve as spatial units for all numeral calculations. In the invention, Voronois approximate "airport catchment geographies"—i.e. the maximum distances individuals would be expected to travel by ground to fly out of an airport or travel by ground from an airport to their final destination. A global view of Voronois weighted by air traffic volume is shown in FIG. 7. Each Voronoi is created around the geographic coordinates of a city with at least one airport and no two Voronoi overlap. The size and shape of each Voronoi is a function of each city's proximity to neighboring cities with at least one airport and its magnitude of air traffic. Given the approximately 4000 cities in the world with airports, a corresponding number of Voronois is used to cover the world's land geography. Although traffic-weighted Voronoi polygons are described to separate the world's land geography into distinct spatial units in this application, other established techniques to generate spatial units may also be used.

Voronoi polygons are known in mathematics study, but their application to the field of invention is thought to be inventive. In particular, when used in combination with other aspects of the invention, is especially advantageous in generating a transportability index, as will be discussed in more detail below. Referring to FIG. 7, there is shown the world geography modeled using Voronoi polygons that apply a weighting factor for airport traffic volume in each city. This way, irrespective of the population size of the city, the effect of travel between cities is determined based on air traffic.

Quantifying the Vulnerability of Cities to Human Pathogens

Connecting awareness of global infectious disease activity with global population mobility via air travel generates insights into the risks of infectious disease importation for any defined area. However, this does not offer insights into the potential local area impact of a pathogen that is introduced from another area of the world. Defining and quantifying the potential local impact to human health, biosecurity, and/or economic activity requires information synthesis across the following four domains, data relating to which the global pathogen risk factors database 25 may be populated with.

Figure 8:
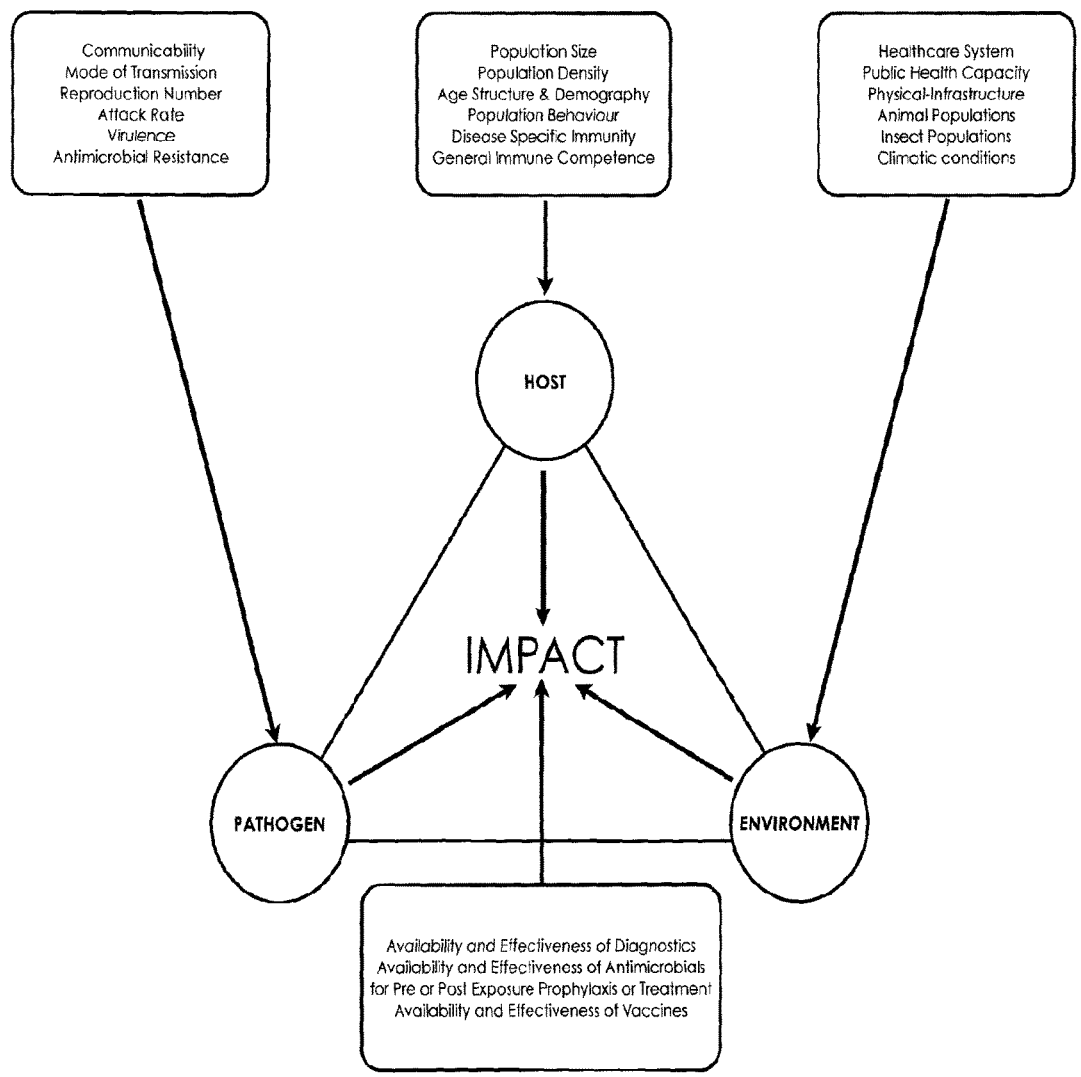
FIG. 8 shows the integration of various factors to define and quantify the potential impact of imported infectious diseases.

The global pathogen risk factors database 25 may be populated with data pertaining to: i) pertinent characteristics of individual pathogens; ii) available medical countermeasures against individual pathogens; iii) pertinent characteristics of the host population; and iv) pertinent characteristics of the environment. The population health impact—that is the vulnerability of a particular city to imported pathogens is a function of the above risk factors. This is depicted graphically in FIG. 8. Pertinent characteristics of individual pathogens may include their communicability, mode of transmission, reproduction number, attack rate, virulence and antimicrobial resistance. Pertinent characteristics of the host population may include the population size, population density, age structure/demographics, population behaviour, disease specific immunity and general immune competence. Pertinent characteristics of the environment may include aspects of the healthcare system, public health capacity, physical infrastructure, animal/insect populations and climatic conditions. Finally, pertinent characteristics of available medical countermeasures may include the availability/effectiveness of diagnostic tools, the availability/effectiveness of antimicrobials for pre or post exposure prophylaxis or treatment, and the availability/effectiveness of vaccines.

In this database, each risk factor is matched to a high quality data source that is a surrogate marker for that risk factor. For example, cholera, which spreads through fecal contamination of food or water, may be matched to the World Bank indicator "Population Access to Improved Sanitation Facilities", which represents the percentage of a population with at least adequate access to excreta disposal facilities that can effectively prevent human, animal, and insect contact with excreta across rural and urban geographies worldwide. Data values pertaining to the pathogen and corresponding medical countermeasures are derived from the expert opinion of clinical infectious disease specialists and databases pertaining to national healthcare resources and systems (e.g. World Bank), whereas data values pertaining to the host population and environment are derived from high quality third-party data sources with global coverage (e.g. the World Health Organization, World Bank, Food and Agriculture Organization of the United Nations, the National Aeronautics and Space Administration, the National Oceanic and Atmospheric Administration, etc.). Data from these sources are pre-processed, stored in computer memory, and updated with the greatest available frequency. In certain instances, data will be updated and saved to the database in real-time (e.g. climate data from satellites).

To produce a standardized vulnerability index for each pathogen across each city worldwide, each set of risk factor values for a pathogen are rescaled between 0 and 1 (lowest to highest risk). This process is achieved by applying a statistical rescaling algorithm to each set of risk factor values using a computer processor, with results saved to a computer readable medium. Where there are multiple sets of risk factors for a given pathogen, each set of risk factor values is independently rescaled, aggregated, and then the sum is rescaled again (i.e. to create a single vulnerability index for each pathogen across each city worldwide). The default rescaling process (where multiple risk factors are involved) is unweighted with optional weighting by users if they deem certain risk factors to be of greater significance than others. Since risk factor values for pathogens continuously change over time, vulnerability indices for each city also change over time. The rescaling process is repeated for each pathogen and its corresponding risk factor values until all pathogens in the invention are processed. The entire process is also repeated at frequent scheduled intervals (e.g. daily) with results saved to memory.

Figure 9:
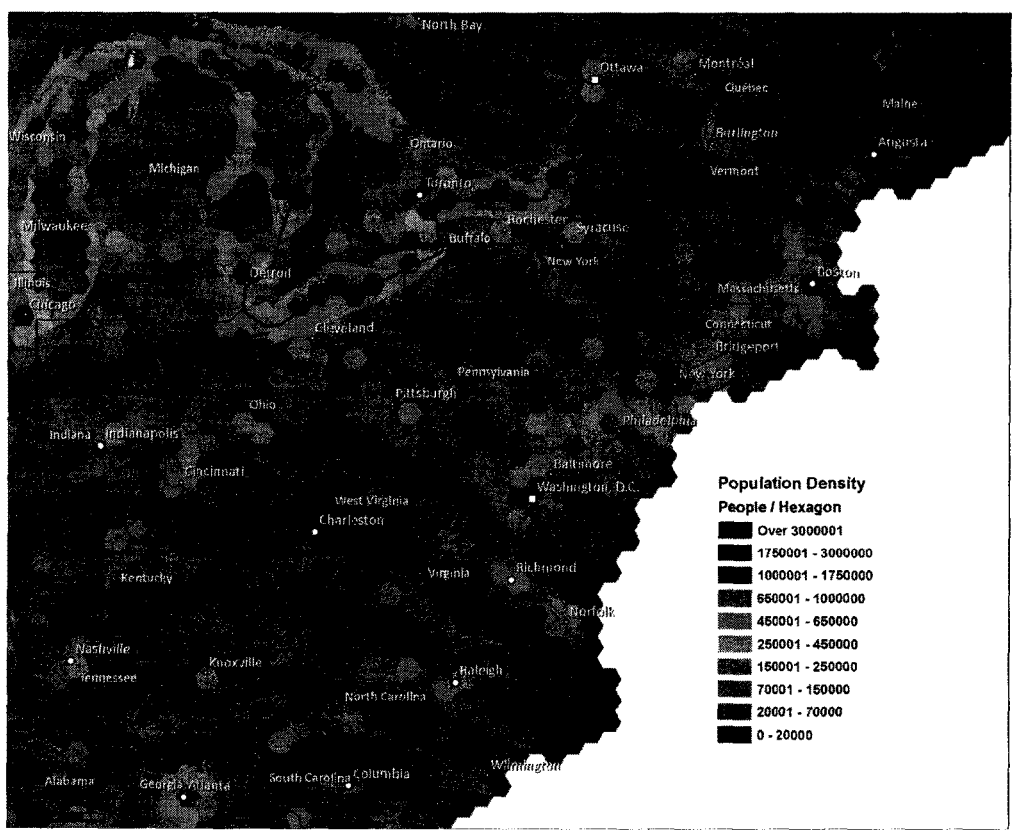
FIG. 9 shows data in hexagons as a potential alternative spatial unit for analysis.

Alternatively, to evaluate local conditions across the above domains within a potential geographic area (e.g., Voronoi or other regional geography such as a state or province), a second, more spatially precise geographic unit of analysis may be used (i.e. hexagons that are 50 km across parallel sides and ~6500 $km^2$ in area—see FIG. 9). At this shape and size, there are 163,000 hexagons that cover the world's land area. While the hexagon shape and stated size is currently used, other polygon shapes and/or sizes may be used in the future. This is because the spatial resolution of data sources may change over time, and smaller spatial units would offer more precise information.

In addition to evaluating the immediate impact of pathogen importation, the invention determines if the unique life cycles of individual pathogens can be completed within a local area, by analyzing data from the global pathogen risk factors database that pertain to each component of the pathogen life cycle. This allows for a determination of whether local conditions are sufficiently present for a pathogen to find a "hospitable" environment, where it can then propagate (e.g., West Nile Virus completed its life cycle and established itself in New York City in 1999 for the first time, after which it spread widely across North America). Schematics of how the risks of infectious disease importation and subsequent local transmission would be evaluated by the invention are shown for pathogens that can spread directly from person-to-person, through contaminated water sources, from animal populations (zoonoses), and insects as examples (see FIGS. 10-13).

For data that is more spatially precise than a single Voronoi polygon or hexagon, information is aggregated (e.g. precipitation data at the 1 $km^2$ level is aggregated up to the Voronoi or hexagon unit level). Conversely, for data that is less spatially precise than a single Voronoi or hexagon, the data is attributed to all Voronois or hexagons within the larger spatial unit (e.g. a report of an epidemic at the state level would be attributed to all Voronois or hexagons within that particular state). The temporal resolution of all data is retained in its most precise form.

A. Pathogen Characteristics

In the system, a catalogue of infectious pathogens is created and used to define features for each pathogen such as the following:
  i. Does the pathogen cause a communicable or a non-communicable disease?
  ii. What is its primary (and if applicable) secondary mode(s) of transmission?
  iii. What living systems and/or environmental factors are necessary for the pathogen to complete its life cycle?
  iv. What is its basic reproduction number (i.e. how easily can it spread)?
  v. How virulent is the pathogen in terms of its morbidity and mortality?
  vi. Is antimicrobial resistance an issue with this pathogen?

Answers to these and related questions are derived from expert domain knowledge of the life cycles, epidemiological patterns, and medical aspects of diagnosing, treating, and preventing different infectious diseases. The system houses a "digital record" of the life cycle of individual pathogens in the global pathogen risk factors database 25. The ability for these pathogens to complete their life cycle and hence increase their local population health impact through local area spread is evaluated using a combination of human, animal, insect, and environmental data. When all of the elements needed for a pathogen to complete its life cycle exist within a local area at a defined point in time, the local area will have met conditions necessary (but not sufficient) for local disease spread.

B. Host Population Characteristics i. Distribution

Information on human population distribution worldwide is accessed via remote sensors on orbiting satellites (e.g. from organizations including the National Oceanic and Atmospheric Administration (NOAA) and the National Aeronautics and Space Administration (NASA)). In the invention, data from the LandScan Land Cover satellite is used to describe the spatial distribution of the world's population.

ii. Demography

Complementing information on human population distribution worldwide, the invention integrates information on human demography. These data are primarily derived from national population censuses. While the content and timing of these censuses vary, the invention focuses on extracting information about potential determinants of infection and health outcomes. These include but are not limited to age, education, income, and housing status. These data are updated either manually or in an automated fashion and integrated into the invention as they become available.

iii. Disease Specific Immunity

National vaccination rates for major vaccine preventable diseases are reported by individual countries or the World Health Organization and offer insights into the extent of population "herd" immunity to specific pathogens. These data are updated either manually or in an automated fashion and integrated into the invention as they become available.

iv. General Immune Competence

Information about general immune competence is incorporated using data from organizations such as the World Health Organization and/or World Bank pertaining to population immunosuppression due to diseases such as HIV-AIDS, malnutrition, and other related factors.

C. Prevention and Response Options

For each pathogen in the system catalogue, information is included about:
  i. Whether a vaccine currently exists to prevent new infections
  ii. Whether the vaccine is broadly accessible to the general population (e.g. polio vaccine) or if it is a special access vaccine that is not widely manufactured (e.g. smallpox vaccine)
  iii. If vaccine access would be immediate or delayed when needed (e.g. influenza vaccine for a novel virus can be delayed by several months)
  iv. If there are pre-exposure prophylaxis options and post-exposure prophylaxis options (e.g. immune globulin or antibiotics)
  v. Whether basic laboratory diagnostic techniques are widely available to establish a diagnosis or if specialized diagnostics are needed
  vi. Whether antimicrobials exist and are effective at preventing and/or attenuating morbidity or mortality from the pathogen D. Environmental Conditions i. Healthcare System The competence of the local healthcare and public health system is an important factor in evaluating the potential local impact of an imported infectious disease. The invention incorporates data elements from the World Bank and World Health Organization such as the amount of financial resources dedicated to healthcare and public health per capita, the number of physicians and nurses per capita, and the number of hospital beds per capita among others.

ii. Physical Infrastructure

The physical environment can have a dramatic affect on the ability for an infectious pathogen to spread. For example, the introduction of cholera into Haiti after the 2010 earthquake had a devastating effect, whereas imported cases of cholera into the United States from Haiti did not result in local transmission. This is because cholera is a water-borne infectious disease and access to clean water and enhanced sanitation facilities markedly differs between the two countries. The invention incorporates selected data elements pertaining to physical infrastructure, which reflect the ability for different pathogens to impact the health of a population through local area spread.

iii. Animal Populations

Human health is increasingly linked with the health of animal populations. An estimated 75% of all new, previously unrecognized human infectious diseases originate from animal populations (e.g. HIV, SARS, "Swine" H1N1 Flu etc.). Under appropriate conditions, infectious diseases normally found in animals can spread to humans. This can occur via direct or indirect human contact with wild animals, livestock, and/or domesticated animals. The invention incorporates selected data elements pertaining to animal populations, which reflect the ability of zoonotic pathogens to impact the health of human populations through transmission from animals.

The Food and Agriculture Organization (FAO) of the United Nations under the

Global Livestock Production and Health Atlas (GLiPHA) program has modeled the worldwide distribution and size of major livestock populations. The invention incorporates these data on the worldwide distribution of poultry, swine, and cattle among other livestock as potential reservoirs for human infectious diseases. Data on the global distribution of wild animals and their migratory patterns may also be integrated into the invention.

iv. Insect Populations

Insects are an integral part of the life cycle for many human infectious diseases. These vector-borne diseases can be spread to humans directly (e.g. *Anopheles* mosquito and the transmission of malaria) or indirectly through animals (e.g. *Ixodes* tick and Lyme disease from rodents). Thus, knowledge of the global distribution and size of insect populations that can serve as vectors for human disease is essential.

The worldwide distribution and size of insect populations has been modeled by a number of organizations, such as the European Centre for Disease Prevention and Control (i.e. VBORNET). These modeled data are derived from local surveys conducted by medical entomologists and public health officials around the world. By integrating these data into the invention alongside human and animal populations, users can gain insights into where living systems coexist (e.g. humans, selected animals and selected insects) and how this creates the conditions necessary for the local area transmission of specific pathogens. Furthermore, the distribution of insect populations is influenced by climatic conditions, which is described below.

v. Climatic Conditions

Climate and the natural environment can have a dramatic impact on infectious disease activity by (i) directly affecting the viability and transmissibility of pathogens (e.g. peak influenza transmission in cold-dry climates), (ii) by altering the reproduction rate of key insect vectors (e.g. increased rain and higher temperatures can accelerate the reproduction of mosquitoes that can then transmit human disease), and/or (iii) by providing the appropriate flora and/or fauna for insect vectors and/or animal reservoirs to survive and propagate.

In the invention, climate data is incorporated from a combination of remote (i.e. satellite) and ground based sensors. Data from these sensors are used to generate real-time information on environmental and climatic conditions worldwide. The following is a list of the main sensors in use with a brief description of each.

AIRS—Atmospheric InfraRed Sensor

NASA operates the AIRS satellite, which provides data on surface air temperature, surface skin temperature, precipitable water, water vapour (relative humidity), sea surface temperature, ozone, and carbon dioxide among others. The invention currently extracts and integrates real-time data pertaining to air temperature and relative humidity (see FIG. 6) since these factors are known to influence infectious disease activity. All values are compared with long-term historic averages.

TRMM—Tropical Rainfall Measurement Mission

The Tropical Rainfall Measuring Mission (TRMM) is a joint mission between NASA and the Japan Aerospace Exploration Agency (JAXA) designed to monitor and study tropical rainfall. These real-time data covers 50 degrees north and south of the equator. Other national datasets are used to produce a global mosaic of real-time precipitation levels. The invention currently extracts and integrates information on rainfall at hourly intervals. All values are compared with long-term historic averages.

GOES—Geostationary Operational Environmental Satellite

There are a number of satellites in the constellation of the GOES system, however the invention is presently using data from the two most current GOES-13 (East) and GOES-15 (West). These satellites have both visible and infrared (IR) sensors for measuring atmospheric moisture, as in, clouds, temperature of clouds, and water vapour. The invention currently uses band-4 of the infrared data to capture atmospheric clouds, which is used as predictor for storm/rainfall intensity. Complementing the GOES satellites, additional data of a similar nature are being extracted and integrated to form a global mosaic from:

EUMETSAT—Operated by European Space Agency, covers Europe and Africa

IODC—European Space Agency, covers India and central Asia

MTSAT—Operated by Japan, covering Eastern Asia and the Pacific

Night Lights DMSP—OLS

The Defense Meteorological Satellite Program (DMSP) Operational Linescan System (OLS) has the capability to detect the nocturnal observation of artificial lighting, which can reflect the degree of urbanization and human population activity. Values are compared with historic averages to understand changes in urbanization.

NDVI—MODIS

NASA operates a remote sensing system called MODIS (Moderate Resolution Imaging Spectroradiometer), which among its sensors can generate NDVI (Normalized Difference Vegetation Index) data. NDVI is used to measure biomass and differences in biomass over time and to long-term normals. This dataset can offer insights into the presence of vegetation needed to support animal and/or insect life that are necessary for the transmission of infectious disease. Values are compared with historic averages to understand environmental changes.

In addition to the use of satellite data to define climatic conditions, combinations of these climatic data are used in the invention to delineate specific geographies where (and when) specific insect vectors for human pathogens would be capable of surviving and consequently transmitting specific human infectious diseases. This approach is used to account for limitations and geographic gaps in vector surveillance and concurrently identify where and when these vectors could establish themselves if introduced into a new environment. Moreover, where available, satellite data are compared with long-term historic averages to evaluate the gradual effects of climate change and urbanization.

As has now been demonstrated, it is possible to model the vulnerability of local areas to individual pathogens based upon combinations of pathogen-specific risk factor values as mentioned above.

Quantifying the Worldwide Activity of Pathogens

A software algorithm may then be applied to compare the geographic boundaries of each city with at least one commercial airport (i.e. each Voronoi) with data on worldwide activity of each pathogen in the global pathogen activity database 30. Data regarding pathogen activity may be derived from an array of complementary infectious disease surveillance systems and sources. The global pathogen activity database is populated with information from the below-identified sources or systems, which are listed by way of example only. Various other existing or future sources are also contemplated.

Official government reporting of notifiable infectious diseases.

Reporting of infectious disease events from medical and public health professional networks (e.g. ProMED-mail).

News of infectious disease events from mass media (e.g. event-based surveillance from GPHIN, HealthMap, MediSys etc.).

Confirmed pathogens from point-of-care diagnostic testing (e.g. from portable diagnostic devices employed in the field).

Suspected pathogens from self-reported syndromes (e.g. via health apps on smartphones and other mobile devices).

Search engine activity (e.g. Google™ Flu Trends).

Social media data (e.g. Twitter™).

Data values from each surveillance source are rescaled so that each city worldwide has an activity value between 0 and 1 (lowest to highest risk). This process is achieved by applying a statistical rescaling algorithm to each set of surveillance input values using a computer processor, with results saved to memory. Where there are multiple sets of surveillance inputs for a pathogen, each set of data is independently rescaled, aggregated, and then the sum is rescaled again (i.e. to create a single activity index for each city worldwide for each pathogen). The rescaling process by default is unweighted with optional weighting if users deem certain surveillance inputs to be of greater significance or reliability than others. Since surveillance input values for pathogens are constantly changing, pathogen activity indices for each city also change over time. The rescaling process is repeated for each pathogen and its corresponding activity values until all pathogens in the invention are processed. The entire process is then repeated at frequent scheduled time intervals (e.g. daily) with results saved to memory.

Further details regarding possible source of surveillance information will now be discussed.

Government-Based

Governmental reporting of infectious disease data is generally considered the most reliable form of surveillance (i.e., also known as indicator-based surveillance). This is because healthcare providers rigorously evaluate patients on clinical grounds, and typically have laboratory evidence that confirms the presence of a particular microbe. However, infectious disease reporting by healthcare providers is only required for officially "notifiable" or "reportable" diseases, as defined by local public health administrative units. These systems are untimely, in terms their ability to make information quickly accessible, largely due to administrative and reporting delays. These delays can be further exacerbated in geographies of the world with limited diagnostic laboratory capabilities and weak public health systems. Furthermore, government suppression of information, which may occur if governments perceive economic repercussions from reporting, can also limit the value of these systems. The invention integrates these infectious disease data, currently with manual updates as new information is released, however future enhancements in government reporting will enable data to be consumed in an automated fashion via the Internet.

Provider-Based

Networks of public health and medical providers around the world can offer valuable global epidemic intelligence. ProMED-mail is an example of an international network where information about infectious disease events or outbreaks is reported via the Internet. The system integrates these infectious disease data through existing web-based channels.

There is a growing movement toward infectious disease diagnostic testing at the point of patient contact. Today, most diagnostic testing is performed in large laboratories that are stationary. However, as point of contact diagnostics evolve and become more accessible, they will inevitably become capable of transferring data via the Internet into large surveillance databases. While this capability is currently in its infancy, it has the potential to be highly accurate and very timely. The invention can integrate these types of infectious disease data in the future when they emerge.

Internet-Based

With the global rise in communication via the Web, a number of systems have emerged that trawl public facing Internet traffic for "chatter" that could signal the early stages of an emerging infectious disease threat (i.e. also known as event-based surveillance). Systems such as the Global Public Health Intelligence Network (GPHIN), HealthMap, and MediSys are among the most well recognized platforms, although there are many others emerging. The advantage of these systems is that they are timelier than official government reporting, and are less impacted by weak public health systems and/or government suppression of information. Conversely, these systems tend to be noisy and distinguishing signal (i.e. a real infectious disease event of public health significance) from background noise (i.e. stories that are inaccurate or not significant) can be problematic. The invention integrates these infectious disease data through existing web-based channels.

The growing worldwide use of the Internet has also created opportunities for large organizations such as Google™ to monitor the nature of browser searches using their search engine. Such information has been used as a surveillance tool for diseases such as influenza (i.e., Google™ Flu Trends) and more recently dengue fever (Google™ Dengue Trends). The system can integrate these infectious disease data via the Internet.

Social Media-Based

The rise of social media for communication can also be a potential source of timely global epidemic intelligence, however these systems can be even noisier than general Internet-based "chatter". Nonetheless, they have proven to be timely sources of information in disaster settings when traditional communication channels and infrastructure have been compromised. A number of infectious disease surveillance systems are increasingly harnessing social media content for epidemic intelligence (e.g. HealthMap). The invention can integrate these infectious disease data via the Internet.

System Data Sources and Content

In the invention, infectious disease surveillance data from existing (and future) systems is integrated using multiple approaches. Web-based data is integrated using standard computing techniques (e.g. data service, Geo-RSS feed etc.) via the Internet, while data from paper-based reports is manually entered into the global pathogen activity database as they become available. All data is collected and integrated into the invention with the greatest level of spatial and temporal resolution available. For each microbe, information is extracted to define the global distribution of infection and disease, burden of infection and disease, seasonal patterns, and special microbial features (e.g. antimicrobial resistance, genotypic profile for virulence etc.). As these information sources evolve and become more accurate, timely, and spatiotemporally precise, the invention will passively enhance its predictive accuracy.

Quantifying Connectivity between Global Geographies

Data on worldwide air travel patterns is stored in the global transport database. This database is populated with worldwide flight schedules data, worldwide airline ticket sales and passenger flight itinerary data, and real-time aircraft-level flight data. Other pertinent travel datasets (e.g. sea based travel from the International Maritime Organization) may also be incorporated for coastal cities as appropriate. For each city (i.e. Voronoi), the scale of inbound connectivity from all other cities (i.e. Voronois) will be calculated using a computer processor. For example, analysis of flight schedules data produce the total number of passenger seats scheduled to arrive from all other cities worldwide via direct flights. These values will then be rescaled between 0 and 1 to create indices of connectivity by flights. The same process will then be repeated for every other city worldwide with results saved to memory. In addition, analysis of passenger ticket sales and flight itineraries data will produce the total number of inbound passengers expected to arrive in a given city from all other cities worldwide. These values will also be rescaled between 0 and 1 to create indices of connectivity by travelers. The same process will then be repeated for every other city worldwide with results saved to memory. Each set of data is independently rescaled, aggregated, and then the sum is rescaled again (i.e. to create a single transportability index for each city as it relates to inbound traffic from each other city worldwide). The rescaling process by default is unweighted with optional weighting if users deem certain forms of travel or travel metrics to be of greater significance than others. Since worldwide travel patterns are continuously evolving, transportability indices for each city also change over time. This process is then repeated at frequent scheduled intervals (e.g. daily) with results saved to memory.

Integrating and Visualizing Data for Forecasting

The invention described herein is unique, not only because of the novel methods used to integrate global infectious disease surveillance, global population mobility, clinical and microbiological features, life cycles, and medical aspects of human pathogens, but also a combination of information systems and technologies pertaining to environmental conditions worldwide.

Technical components of the invention include: (i) a geodatabase that houses and continuously incorporates new data across each of the aforementioned content geographies, (ii) a web-enabled GIS application that continuously runs spatial and statistical analyses as described, and (iii) physical and/or virtual (i.e. cloud) computing hardware where all geoprocesses and statistical operations are performed. Outputs from the system are then disseminated via the Internet for consumption by end-users in any given geography worldwide.

Finally, having obtained, stored and processed the relevant data in each of the databases described, the invention contemplates integrating these data for the purposes of processing, and for presenting in a manner that permits for the results desired by the invention, as described above.

After the above processes are completed, the following values are saved to memory and used to generate forecasting reports:

1. A rescaled vulnerability index for each pathogen across each city (i.e. Voronoi) worldwide. This is saved as a series of data tables (one for each pathogen in the invention) populated with vulnerability indices by cities.

2. A rescaled activity index for each pathogen across each city worldwide. This is saved as a series of data tables (one for each pathogen in the invention) populated with activity indices by cities.

3. A rescaled transportability index for each city in terms of its inbound connectivity to every other city worldwide. This is saved as a matrix populated by inbound transportability indices for each unique city pair worldwide.

The three sets of indices are then integrated to produce forecasting reports specific to each pathogen and city in the world. Reports comprise a scatterplot of rescaled pathogen activity indices for each city worldwide (i.e. with values ranging between 0 and 1) on the y-axis and inbound transportability indices for each corresponding city worldwide (i.e. with values ranging between 0 and 1) on the x-axis. End-users from (or interested in) a given city receive reports sorted in order of highest to lowest pathogen vulnerability. Users are also presented with information indicating whether each pathogen is, or is not already endemic to their city of their interest.

Figure 10:
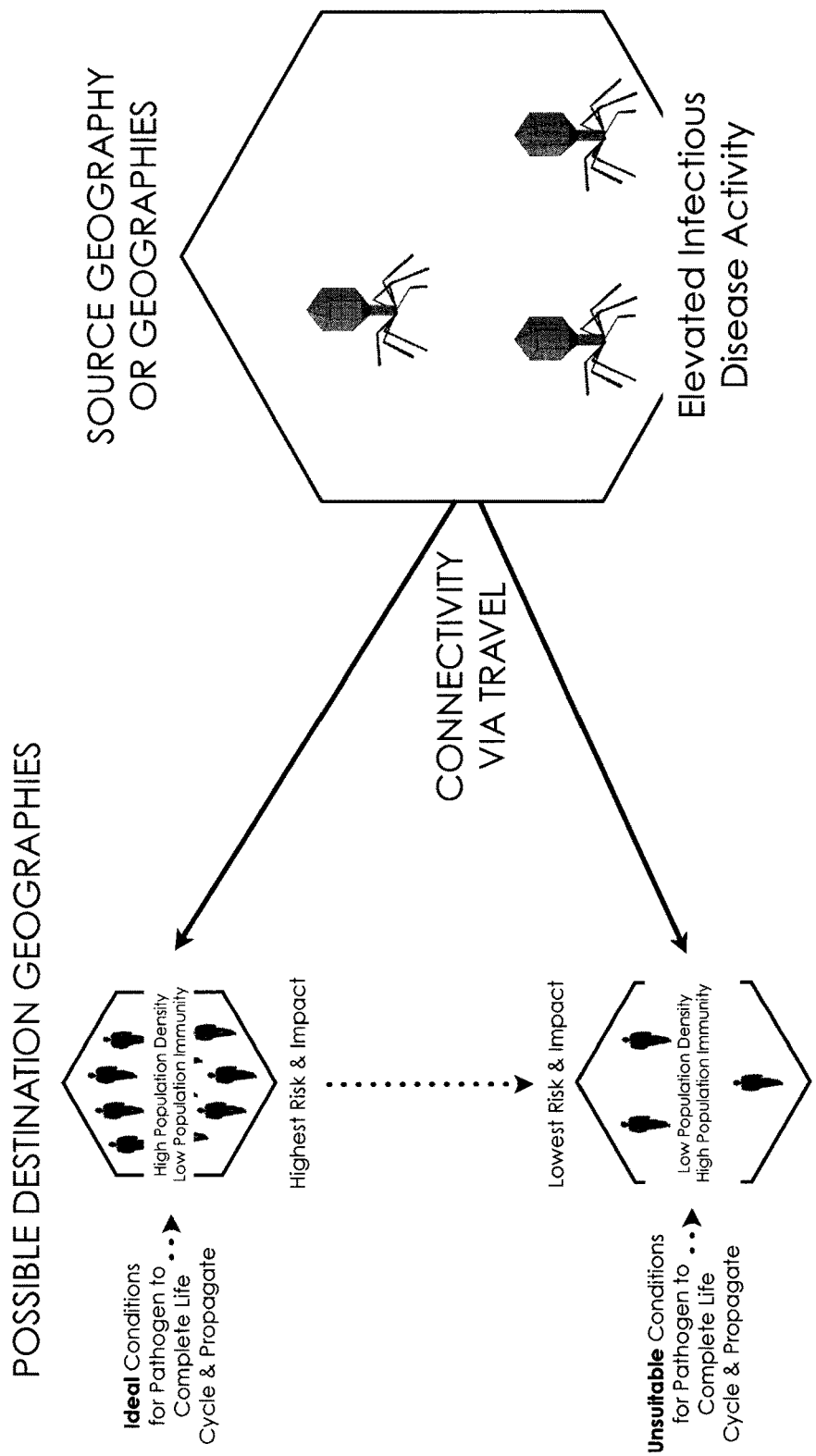
FIG. 10 is a schematic diagram for anticipating the introduction and local spread of infectious diseases that are transmitted directly from person to person.
Figure 11:
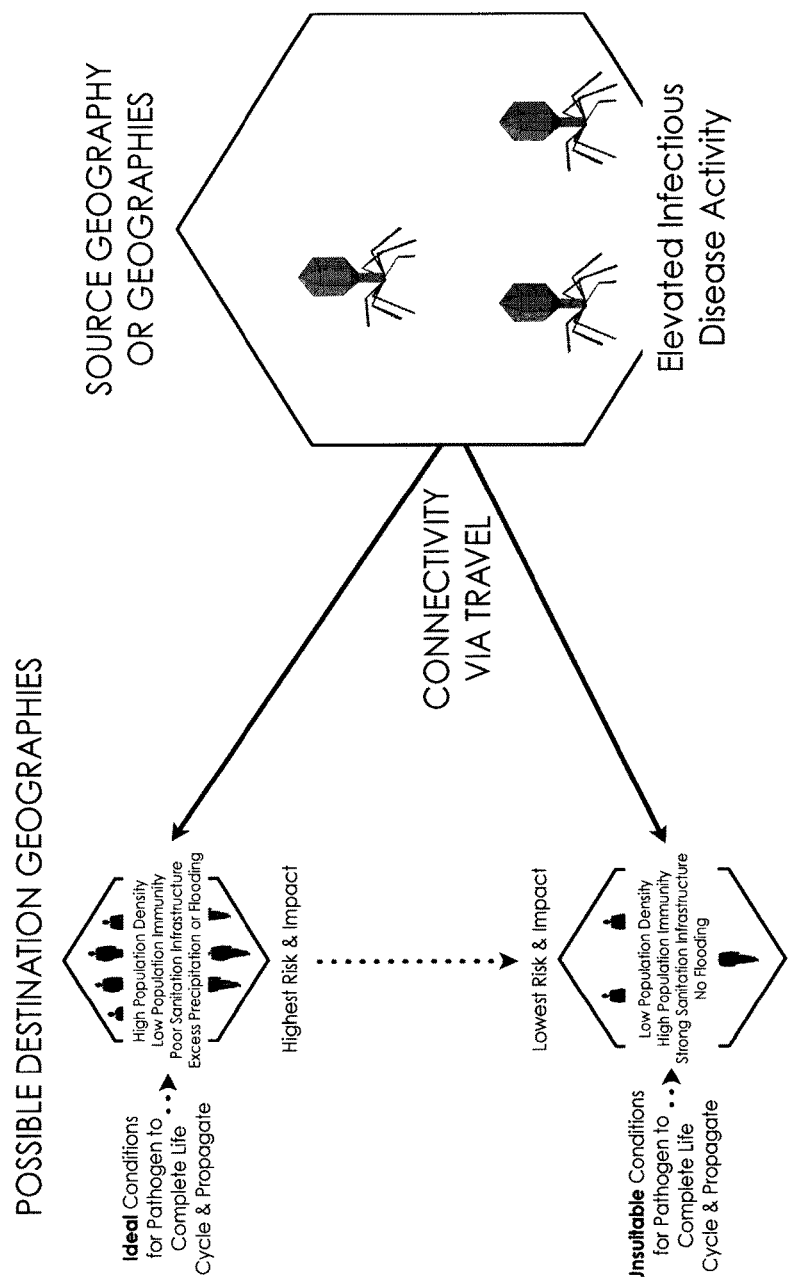
FIG. 11 is a schematic diagram for anticipating the introduction and local spread of water-borne infectious diseases.
Figure 12:
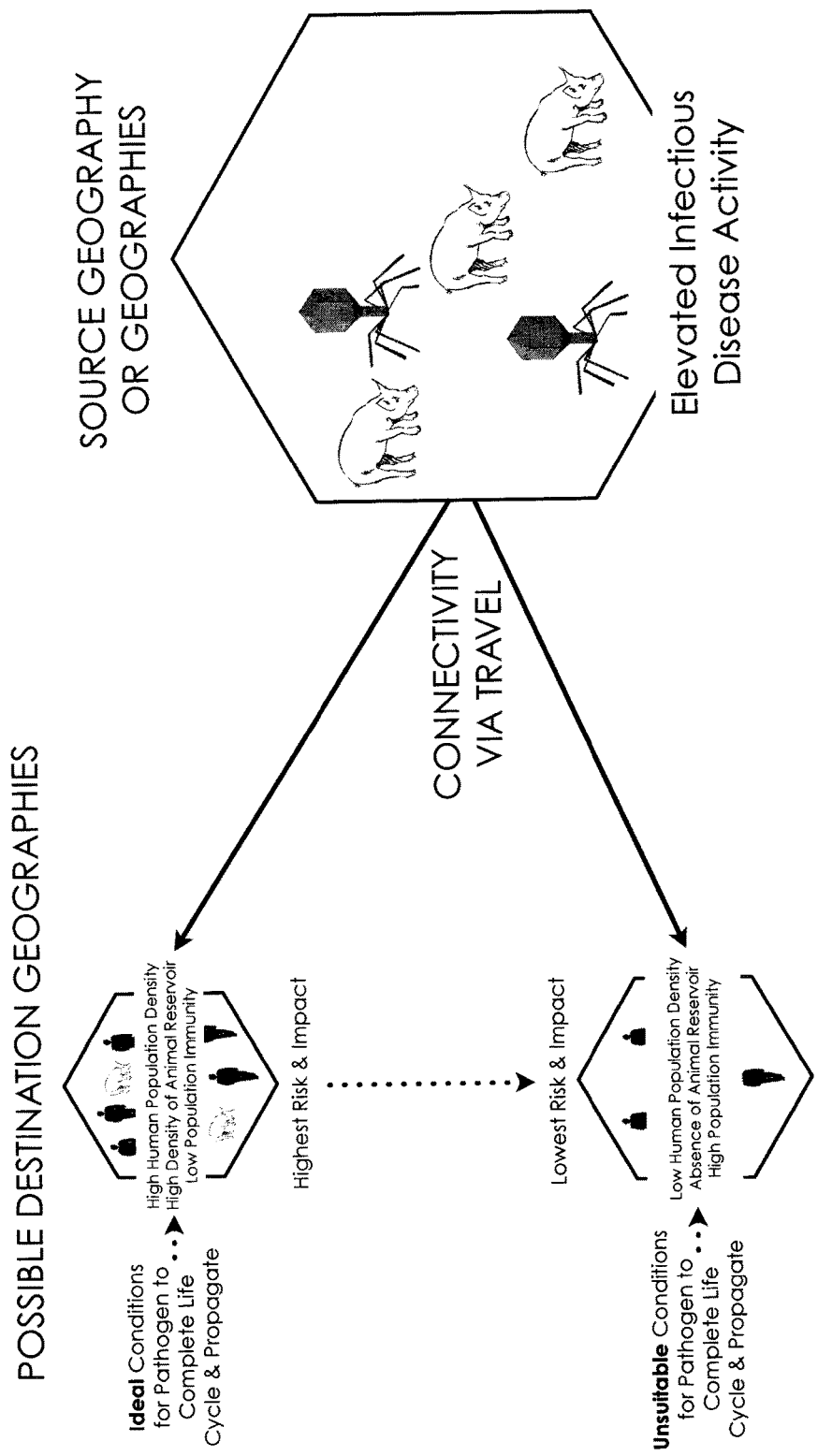
FIG. 12 is a schematic diagram for anticipating the introduction and local spread of zoonotic infectious diseases.
Figure 13:
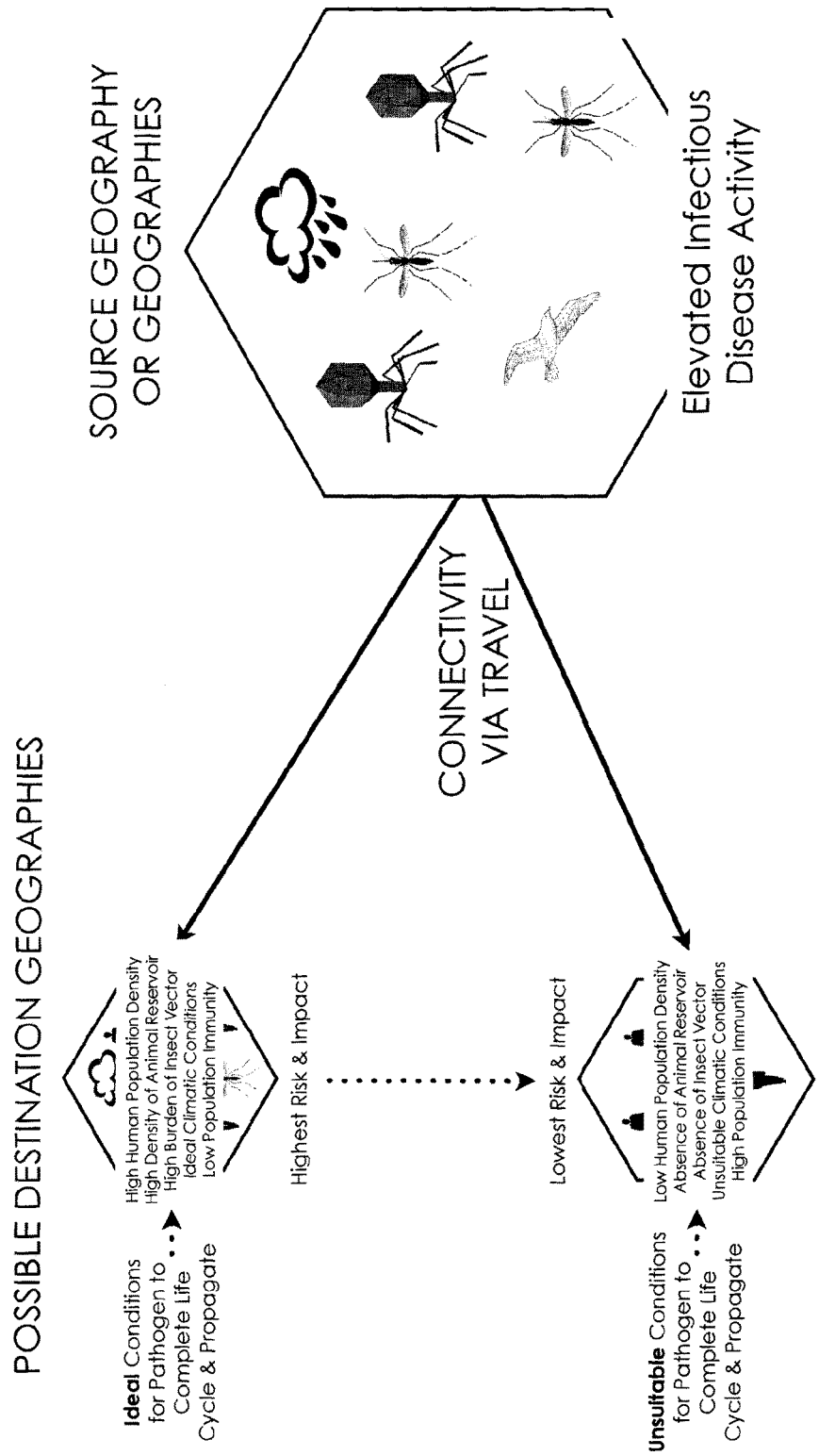
FIG. 13 is a schematic diagram for anticipating the introduction and local spread of vector-borne infectious diseases.

Supplementing the scatter plots are tables that comprise the same data as described above, but which offer end users greater flexibility in managing and organizing the information (e.g. sorting, filtering, exporting etc.). Both the scatter plots and tables are linked through a geodatabase to a map that outlines all of the Voronoi polygons worldwide. Thus, users are able to visualize the spatial distribution of data from the scatter plots and tables to facilitate a greater understanding of the information. Since the entire process is repeated at frequent scheduled intervals (e.g. daily), reports can be generated on a near-real-time basis. By accessing historical data on these indices, results may be visualized dynamically over time. Thus, reports are designed to help decision-makers better anticipate infectious disease risks before they occur so that they may take proactive measures to prevent or mitigate the potential health, security, and economic consequences of pathogen importation. FIGS. 10-13 schematically illustrate the highest risk and impact versus the lowest risk and impact of different categories of pathogens, which result could be directly linked to the method carried out by the system as herein described. For example, FIG. 10 shows that cities with high population densities and low population immunities to particular pathogens present the ideal conditions for infectious diseases that are transmitted directly from person-to-person to be manifested, and become a public health concern. FIG. 11 shows ideal and unsuitable conditions for pathogens leading to water-borne infectious diseases. FIG. 12 shows ideal and unsuitable conditions for the spread of zoonotic infectious diseases, and FIG. 13 shows ideal and unsuitable conditions for the spread of vector-borne infectious diseases. These schematics can be used to map the results of the method of the invention against, by applying index scores as herein described.

The above-described embodiment is intended to be examples of the present invention and alterations and modifications may be effected thereto, by those of skill in the art, without departing from the scope of the invention that is defined solely by the claims appended hereto.

ILLUSTRATIVE EXAMPLE

Figure 14:
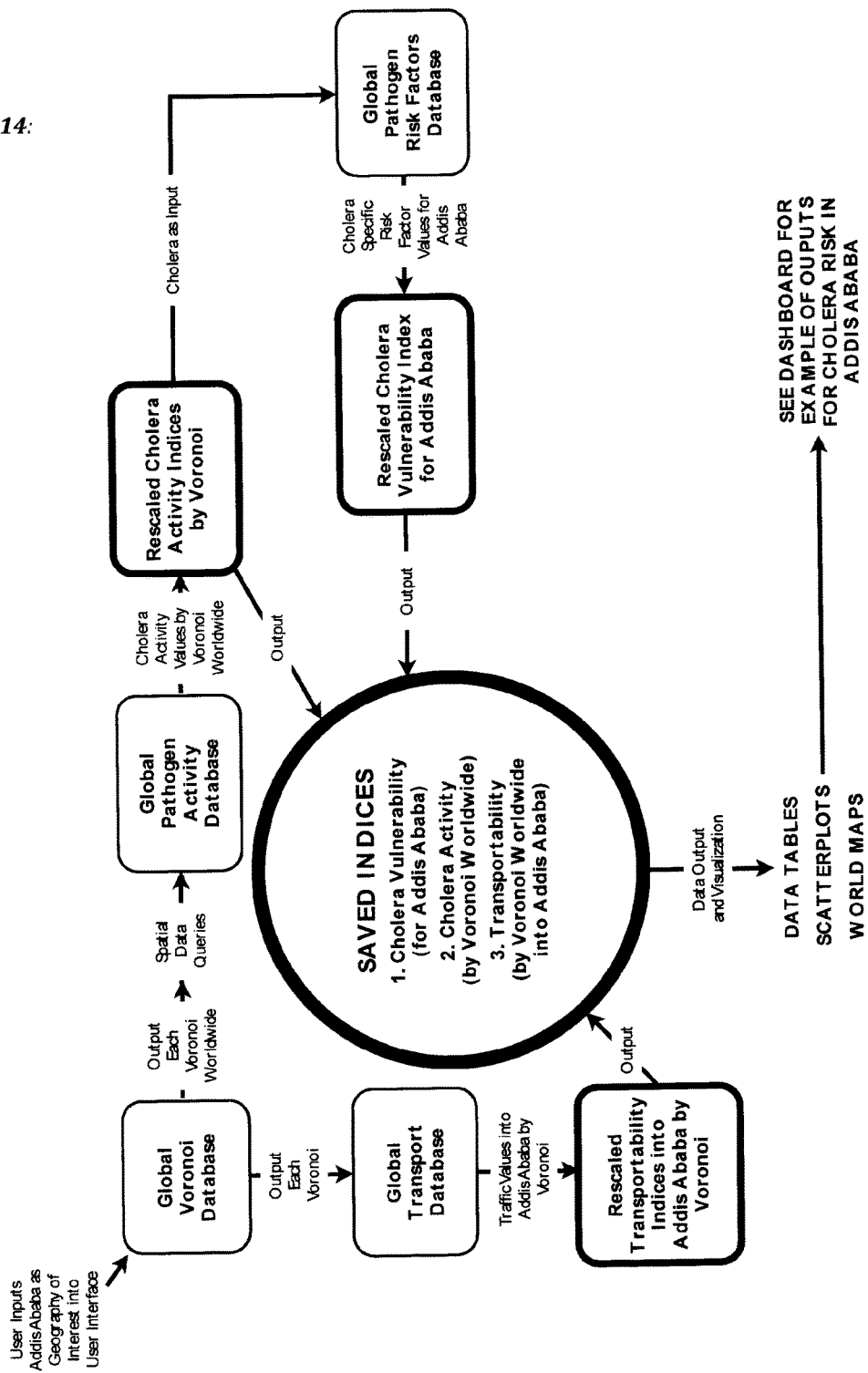
FIG. 14 shows the method to generate a forecast for the infectious disease cholera.

To demonstrate how the invention operates for a specific pathogen, a sample forecast for the infectious disease cholera in the city of Addis Ababa, Ethiopia is shown. FIG. 14 demonstrates the computing processes in which the cholera vulnerability index for Addis Ababa, worldwide cholera activity indices, and transportability indices from all cities worldwide into Addis Ababa are calculated. FIG. 15 demonstrates risk factor data values pertaining to cholera vulnerability by city (i.e. Voronoi) as a saved table, whereas FIG. 16 demonstrates the transformation of these data into rescaled values that are then aggregated. FIG. 17 demonstrates cholera activity values by city worldwide, whereas FIG. 18 demonstrates the transformation of these data into rescaled values that are then aggregated.

Figure 22:
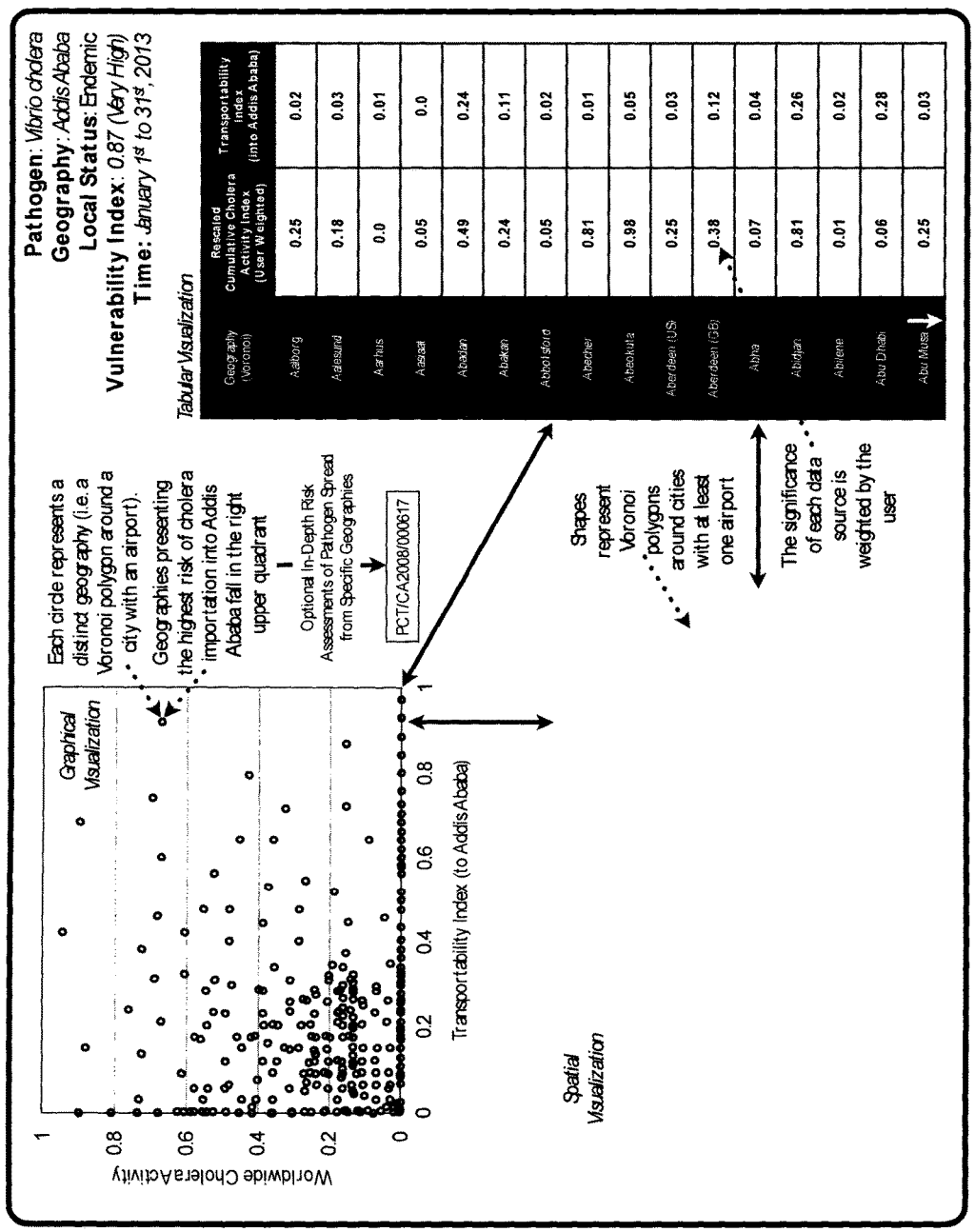
FIG. 22 is a sample forecast report for cholera risks to Addis Ababa for the month of January 2013.

FIG. 19 demonstrates airline passenger values between combinations of city pairs, whereas FIG. 20 demonstrates the transformation of these data into rescaled values. FIG. 21 demonstrates rescaled cumulative cholera activity indices (that have been weighted by an end-user) alongside transportability indices into Addis Ababa. The combination of these two factors is used to identify source cities posing the greatest potential risk of cholera importation into Addis Ababa. FIG. 22 demonstrates a hypothetical dashboard of a cholera forecast for Addis Ababa including a combination of integrated tables, scatterplots, and maps.

I claim:

1. A method for preventing the spread of global infectious diseases across a plurality of areas, the method comprising:
   providing on a non-transitory computer readable medium a global pathogen risk factors database having data stored therein related to local area vulnerability of individual human pathogens across said plurality of areas;
   providing on the non-transitory computer readable medium a global pathogen activity database having data stored therein related to the activity of said individual human pathogens in said plurality of areas;
   providing on the non-transitory computer readable medium a global transport database having data stored therein related to travel patterns in across said plurality of areas;
   processing, by a computer system, data on said global pathogen risk factors database said global pathogen activity database and said global transport database to generate a pathogen vulnerability index, a pathogen activity index and a transportability index;

modeling, by said computer system, each of said plurality of areas as a spatial unit, and storing on the non-transitory computer readable medium a unique spatial unit for each of said plurality of areas having at least one airport or seaport; said spatial unit weighted by traffic volume of said at least one airport or seaport;

processing, by said computer system, each of said pathogen vulnerability index, said pathogen activity index, and said transportability index to generate a risk indicator indicative of the local area risk of individual global infectious diseases; and providing said risk indicator to at least one of said plurality of areas, so that proactive measures are taken to prevent or mitigate said global infectious diseases to said at least one of said plurality of areas.

2. The method according to claim 1, wherein said plurality of areas comprises all cities in the world having at least one airport or seaport, such that there is stored a unique spatial unit for each said city with at least one airport or seaport.

3. The method according to claim 2, wherein each said spatial unit is a function of each city's proximity to neighboring cities with at least one airport or seaport and of the magnitude of traffic at said at least one airport or seaport.

4. The method according to claim 3, wherein said spatial unit is a Voronoi polygon.

5. The method according to claim 1, further comprising normalizing by said computer system said pathogen vulnerability index, said pathogen activity index and said transportability index.

6. The method according to claim 5, wherein said normalizing comprises scaling to a value between 0 and 1.

7. The method according to claim 1, wherein said data stored on said global pathogen risk factors database includes a list of individual risks and a risk factor applied to each of said individual risks; and wherein said generating said risk indicator comprises generating a pathogen vulnerability index which further comprises generating a risk score as one of an average and a weighted average of said individual risks.

8. The method according to claim 7, wherein said list of individual risks and risk factors are further provided for each pathogen in said group of human pathogens.

9. The method according to claim 1, wherein said data stored on said global pathogen activity database includes data on the activity of pathogens derived from one or more different sources.

10. The method according to claim 9, wherein said one or more different sources are selected from the group comprising official government reporting, reporting from medical and public health professional networks, mass media news sources, diagnostic devices deployed in a particular geography, mobile devices, Internet search activity and social media data.

11. The method according to claim 10, wherein said generating a pathogen activity index comprises assigning an index to each said one or more different surveillance sources for each pathogen and calculating an average or a weighted average of each said assigned index.

12. The method according to claim 1, wherein said transportability index is calculated by assigning a geography index between each and every city based on the number of inbound travelers expected to arrive.

13. A computer system for preventing the spread of global infectious diseases across a plurality of areas comprising:
a processor;
a memory storing processor executable instructions;
a non-transitory computer readable medium having a global pathogen risk factors database with data stored therein related to local area vulnerability of a group of human pathogens across a plurality of areas;
a non-transitory computer readable medium having a global pathogen activity database with data stored therein related to the activity of said group of human pathogens in said plurality of areas; and
a non-transitory computer readable medium having a global transport database including data stored therein related to travel patterns across said plurality of areas;
wherein the processor executes said instructions to:
model each of said plurality of areas as a spatial unit, and storing on a computer readable medium a unique spatial unit for each of said plurality of areas having at least one airport or seaport, said spatial unit, weighted by traffic volume of said at least one airport or seaport;
process data on each of said global pathogen risk factors database, said global pathogen activity database, and said global transport database to generate a pathogen vulnerability index, a pathogen activity index and a transportability index;
generate a risk metric indicative of the local area risk of global infectious diseases, based on each of said pathogen vulnerability index, said pathogen activity index and said transportability index; and
provide said risk indicator to at least one of said plurality of areas, so that proactive measures are taken to prevent or mitigate said global infectious diseases to said at least one of said plurality of areas.

14. The system according to claim 13, wherein said plurality of areas comprises all cities in the world having at least one airport or seaport, such that there is stored a unique spatial unit for each said city with at least one airport or seaport.

15. The system according to claim 14, wherein said transportability index is calculated by assigning a geography index between each and every city based on the number of inbound travelers expected to arrive.

16. The system according to claim 13, wherein each said spatial unit is a function of each city's proximity to neighboring cities with an airport or seaport and of its magnitude of air traffic.

17. The system according to claim 13, wherein said spatial unit is a Voronoi polygon.

18. The system according to claim 13, further comprising computer executable instructions executed by said computer system for normalizing by said computer system said pathogen vulnerability index, said pathogen activity index and said transportability index.

19. The system according to claim 18, wherein said normalizing comprises scaling to a value between 0 and 1.

20. The system according to claim 13, wherein said data stored on said global pathogen risk factors database related to a local area vulnerability of a group of human pathogens includes a list of individual risks and a risk factor applied to each of said individual risks; and wherein said generating a pathogen vulnerability index comprises generating a risk score as one of an average and a weighted average of said individual risks.

21. The system according to claim 20, wherein said list of individual risks and risk factors are further provided for each pathogen in said group of human pathogens.

22. The system according to claim 13, wherein said data stored on said global pathogen activity database includes data on the activity of pathogens derived from one or more different sources.

23. The system according to claim 22, wherein said one or more different sources are selected from the group comprising official government reporting, reporting from medical and public health professional networks, mass media news sources, diagnostic devices deployed in a particular geography, mobile devices, Internet search activity and social media data.

24. The system according to claim 23 wherein said generating a pathogen activity index comprises assigning an index to each said one or more different surveillance sources for each pathogen and calculating an average or a weighted average of each said assigned index.

* * * * *